U S012417851B2

United States Patent
Carter et al.

(10) Patent No.: US 12,417,851 B2
(45) Date of Patent: *Sep. 16, 2025

(54) HYBRID MEDIA DISTRIBUTION FOR TELEHEALTH SESSIONS

(71) Applicant: Proximie Inc., Boston, MA (US)

(72) Inventors: Christopher Richard Carter, Haywards Heath (GB); Aurelijus Vizgaitis, Pocasset, MA (US)

(73) Assignee: Proximie Inc., Boston, MA (US)

( * ) Notice: Subject to any disclaimer, the term of this patent is extended or adjusted under 35 U.S.C. 154(b) by 23 days.

This patent is subject to a terminal disclaimer.

(21) Appl. No.: 18/372,401

(22) Filed: Sep. 25, 2023

(65) Prior Publication Data

US 2024/0249849 A1  Jul. 25, 2024

Related U.S. Application Data

(63) Continuation-in-part of application No. 18/207,343, filed on Jun. 8, 2023, now Pat. No. 12,316,886.

(Continued)

(51) Int. Cl.
*G16H 80/00* (2018.01)
*G16H 40/67* (2018.01)

(52) U.S. Cl.
CPC ............. *G16H 80/00* (2018.01); *G16H 40/67* (2018.01)

(58) Field of Classification Search
CPC ...... H04N 21/321; H04N 5/91; H04N 21/237; H04N 21/2402; G16H 80/00; G16H 40/67

(Continued)

(56) References Cited

U.S. PATENT DOCUMENTS 6,237,022 B1 * 5/2001 Bruck ................... H04L 67/306
709/200
6,510,553 B1 * 1/2003 Hazra ................ H04N 21/4622
348/565

(Continued)

FOREIGN PATENT DOCUMENTS

KR         101022213 B1      3/2011

OTHER PUBLICATIONS

PCT Patent Application PCT/US2024/012356 International Search Report and Written Opinion of the International Searching Authority issued Sep. 24, 2024.

(Continued)

*Primary Examiner* — An Son P Huynh
(74) *Attorney, Agent, or Firm* — Erise IP, P.A.

(57) ABSTRACT

Systems, methods, and computer-readable media for hybrid media distribution in a telehealth session are disclosed. A telehealth session may comprise a video conferencing session between local participants in a first location, such as an operating room, and remote participants in a second location distinct from the first location. The remote participants may connect to the telehealth session via a remote server. The local participants may connect to the telehealth session via a local server disposed in the first location. The local server may forward data received from devices in the first location to the remote server. Prior to forwarding the data, the local server may obscure portions of the data to protect the privacy of the data, such as the face of a patient. The remote server may then broadcast the obscured data to the remote participants.

20 Claims, 9 Drawing Sheets

Related U.S. Application Data

(60) Provisional application No. 63/440,539, filed on Jan. 23, 2023.

(58) Field of Classification Search
USPC .................................................... 725/105
See application file for complete search history.

(56) References Cited

U.S. PATENT DOCUMENTS

| | | | |
|---|---|---|---|
| 6,625,750 B1 | 9/2003 | Duso et al. | |
| 6,937,730 B1* | 8/2005 | Buxton | H04N 21/4627 348/E7.071 |
| 7,349,029 B1* | 3/2008 | Chou | H04N 7/0112 348/E7.015 |
| 7,734,908 B1 | 6/2010 | Kung et al. | |
| 9,576,106 B2 | 2/2017 | Ahmad | |
| 9,621,953 B1* | 4/2017 | Holcomb | H04N 21/8456 |
| 9,769,368 B1* | 9/2017 | Morford | H04N 23/617 |
| 10,088,983 B1* | 10/2018 | Qaddoura | H04N 21/23439 |
| 10,219,014 B2* | 2/2019 | Van Dusen | H04N 21/238 |
| 10,410,000 B1 | 9/2019 | Ghafourifar et al. | |
| 10,812,598 B2* | 10/2020 | Gero | H04L 65/4015 |
| 11,317,134 B1* | 4/2022 | Barnett | H04N 21/23424 |
| 11,606,582 B2* | 3/2023 | Du | H04N 21/2187 |
| 11,684,488 B2* | 6/2023 | Roh | A61B 5/294 606/1 |
| 11,991,413 B2* | 5/2024 | Gupta | H04N 21/44204 |
| 2007/0157281 A1* | 7/2007 | Ellis | H04N 21/4147 725/74 |
| 2007/0248261 A1* | 10/2007 | Zhou | G06T 19/006 382/154 |
| 2009/0232202 A1* | 9/2009 | Chen | H04N 21/234381 375/E7.126 |
| 2010/0027663 A1* | 2/2010 | Dai | H04N 19/48 375/E7.123 |
| 2010/0145794 A1* | 6/2010 | Barger | G06F 16/9535 715/205 |
| 2010/0208133 A1* | 8/2010 | Crabb | H04N 5/147 348/E7.003 |
| 2011/0069940 A1* | 3/2011 | Shimy | H04N 21/4532 386/296 |
| 2011/0078717 A1* | 3/2011 | Drummond | H04N 21/4821 715/764 |
| 2012/0114118 A1* | 5/2012 | Verma | H04N 21/8456 380/42 |
| 2012/0311635 A1* | 12/2012 | Mushkatblat | H04N 21/485 725/43 |
| 2013/0031582 A1* | 1/2013 | Tinsman | H04N 21/4316 725/36 |
| 2013/0147948 A1* | 6/2013 | Higuchi | G01B 11/14 348/135 |
| 2013/0173765 A1* | 7/2013 | Korbecki | H04N 21/42209 709/221 |
| 2013/0201316 A1* | 8/2013 | Binder | H04L 67/12 701/2 |
| 2014/0068692 A1* | 3/2014 | Archibong | H04N 21/6334 725/116 |
| 2014/0282777 A1 | 9/2014 | Gonder et al. | |
| 2014/0368668 A1* | 12/2014 | Sasabuchi | G01S 13/931 348/187 |
| 2015/0015690 A1* | 1/2015 | Roh | G10L 15/26 348/77 |
| 2015/0256790 A1* | 9/2015 | Priest | H04N 5/268 348/441 |
| 2016/0182596 A1* | 6/2016 | Ralph | H04L 67/52 709/219 |
| 2016/0323643 A1* | 11/2016 | Panchaksharaiah | H04N 21/4753 |
| 2017/0337652 A1* | 11/2017 | Sarin | H04N 1/4493 |
| 2018/0122506 A1 | 5/2018 | Grantcharov et al. | |
| 2018/0246768 A1* | 8/2018 | Palermo | G06F 9/5072 |
| 2019/0037247 A1* | 1/2019 | Hodge | H04N 21/2743 |
| 2019/0089614 A1* | 3/2019 | Tang | H04W 72/543 |
| 2019/0125459 A1* | 5/2019 | Shelton, IV | G16H 40/63 |
| 2019/0191209 A1* | 6/2019 | Harb | H04N 21/4825 |
| 2019/0215541 A1* | 7/2019 | Di Pietro | H04L 63/205 |
| 2019/0253742 A1 | 8/2019 | Garten et al. | |
| 2019/0310819 A1* | 10/2019 | Xu | G16H 80/00 |
| 2019/0320445 A1* | 10/2019 | Panigrahi | H04W 24/08 |
| 2020/0021629 A1 | 1/2020 | Vuong | |
| 2020/0049966 A1* | 2/2020 | Brace | G02B 21/0052 |
| 2020/0053280 A1* | 2/2020 | Han | H04N 19/132 |
| 2020/0106708 A1* | 4/2020 | Sleevi | H04L 65/80 |
| 2020/0126645 A1* | 4/2020 | Robbins | H04L 63/10 |
| 2020/0274641 A1* | 8/2020 | Liu | H04L 41/5025 |
| 2020/0389684 A1 | 12/2020 | Grover | |
| 2021/0037295 A1* | 2/2021 | Strickland | H04N 21/435 |
| 2021/0343404 A1 | 11/2021 | Hunt et al. | |
| 2021/0399911 A1 | 12/2021 | Jorasch et al. | |
| 2022/0052815 A1* | 2/2022 | Li | H04W 28/0252 |
| 2022/0054008 A1* | 2/2022 | Venkatraman | G16H 50/70 |
| 2022/0096164 A1* | 3/2022 | Jarc | A61B 34/20 |
| 2022/0122735 A1* | 4/2022 | Sherkat | G06N 3/04 |
| 2022/0133241 A1* | 5/2022 | Jones | A61B 5/1032 600/485 |
| 2022/0141500 A1* | 5/2022 | Du | H04N 21/2542 725/116 |
| 2022/0189626 A1* | 6/2022 | DeBates | G16H 30/40 |
| 2022/0264002 A1* | 8/2022 | Imai | H04N 23/611 |
| 2022/0353468 A1 | 11/2022 | Walia et al. | |
| 2022/0375620 A1* | 11/2022 | Scheib | A61B 34/30 |
| 2022/0386313 A1* | 12/2022 | Dickie | A61B 8/565 |
| 2022/0413489 A1* | 12/2022 | Nakano | H04W 4/44 |
| 2023/0128027 A1* | 4/2023 | Yamane | H04N 7/0127 348/143 |
| 2023/0146947 A1* | 5/2023 | Shelton, IV | A61B 17/1285 606/144 |
| 2023/0216947 A1* | 7/2023 | Bernardi | H04L 67/10 713/150 |
| 2023/0368887 A1* | 11/2023 | Roh | G16H 40/67 |
| 2023/0409749 A1* | 12/2023 | Li | H04N 21/4318 |
| 2024/0064355 A1* | 2/2024 | Marten | H04N 21/262 |
| 2024/0135661 A1* | 4/2024 | Kim | G06F 3/016 |
| 2024/0212458 A1* | 6/2024 | Nelson | G07F 17/3225 |
| 2025/0006376 A1 | 1/2025 | Soori-Arachi | |

OTHER PUBLICATIONS

U.S. Appl. No. 18/207,343 Non-Final Office Action issued Jul. 18, 2024.
U.S. Appl. No. 18/207,343 Final Office Action issued Nov. 1, 2024.
U.S. Appl. No. 18/418,805, Non-Final Office Action issued Jul. 16, 2025.

* cited by examiner

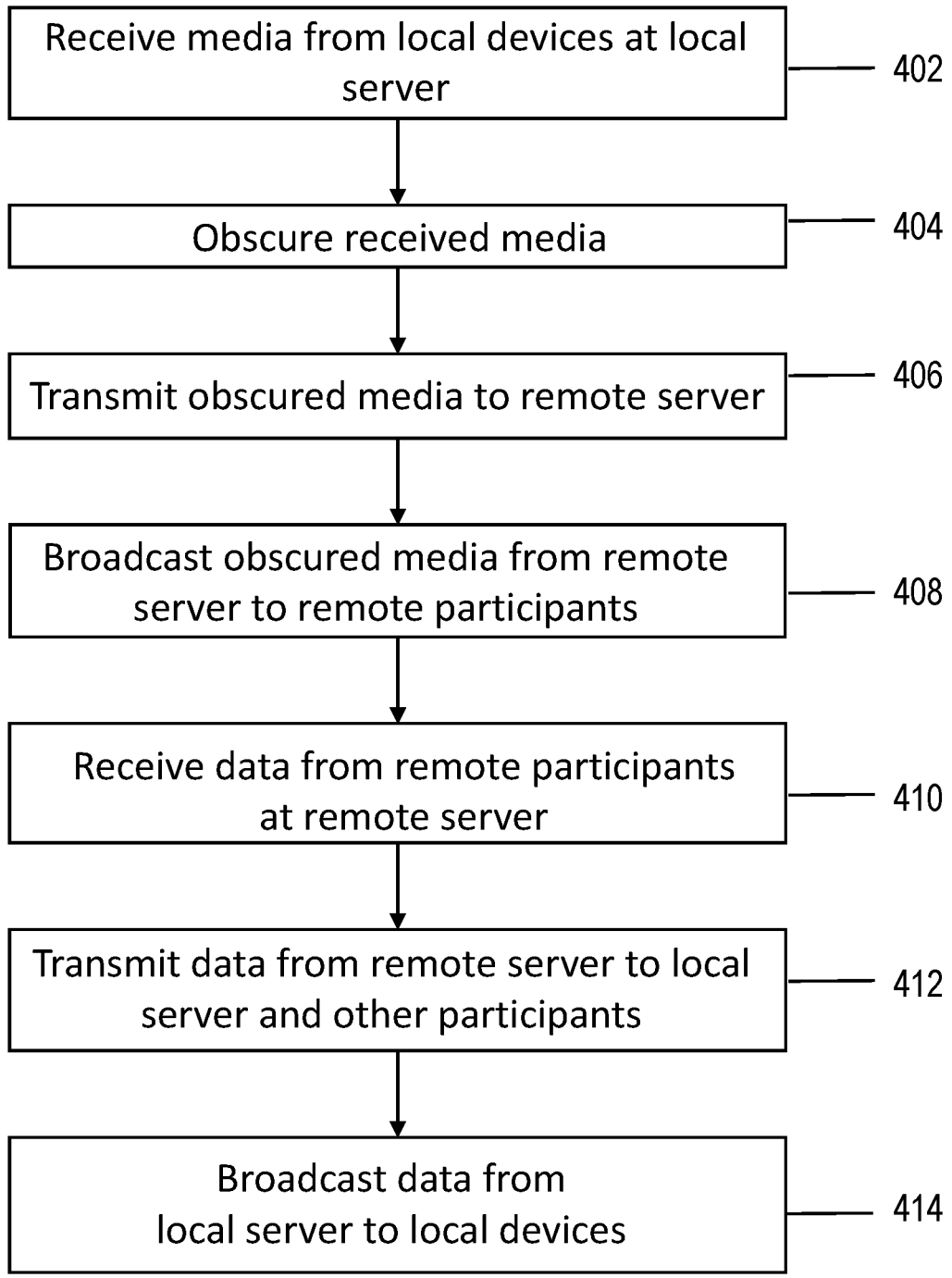
FIG. 4      400

HYBRID MEDIA DISTRIBUTION FOR TELEHEALTH SESSIONS

CROSS-REFERENCE TO RELATED APPLICATIONS

This non-provisional patent application is a continuation-in-part and claims prior benefit, with regard to all common subject matter, of earlier-filed U.S. patent application Ser. No. 18/207,343 ("the '343 Application"), filed Jun. 8, 2023, and entitled "HYBRID MEDIA DISTRIBUTION FOR TELEHEALTH SESSIONS". The '343 application claims priority to earlier-filed U.S. Provisional Patent Application No. 63/440,539, filed Jan. 23, 2023, and entitled "HYBRID MEDIA DISTRIBUTION FOR TELEHEALTH SESSIONS". The identified '343 non-provisional patent application and '539 provisional patent application are hereby incorporated by reference in their entireties into the present application.

BACKGROUND

1. Field

Embodiments of the present disclosure relate to telehealth. More specifically, embodiments of the present disclosure relate to hybrid media distribution using both a local server located in an operating room and cloud-based servers to facilitate a telehealth session.

2. Related Art

Telehealth involves the remote practice of medicine such that a medical practitioner can communicate with a patient when the medical practitioner and the patient are not in the same location. Telehealth is often carried out using video conference techniques, such as a WebRTC video conference. Telehealth technology can enable a medical practitioner, such as a surgeon, to remotely participate in a medical operation. For example, a patient may need a complex brain surgery performed. An expert on the brain surgery may be located in a separate country from where the surgery is taking place. Using telesurgery techniques, the remote expert can video conference into the surgery while the surgery is taking place and provide assistance to the surgeon performing the surgery.

When performing a telesurgery, cameras capture video of the operation being performed and stream the video as part of the video conference. It is generally desirable to use wireless cameras to reduce the trip hazard associated with wired devices in the operating room and the need to sanitize the wiring. Accordingly, wireless and IP cameras that stream video data directly to a hosting server for the telehealth session are often used. However, WebRTC clients cannot detect the wireless cameras as native during a video conferencing session in order to enable a localized preview of the session before the data is broadcast to other participants. Enabling a localized preview allows for the data to be manipulated before being sent to video conference participants, which may be important in telehealth applications when the patient's privacy must be protected. Thus, if a localized preview of the video data is not provided, the data cannot be manipulated (i.e., obscured) before the data leaves the operating room.

Further, it is often desirable to create a recording of the telehealth surgery for later playback. For example, the recording may be useful for later use as a lecture tool to medical students. However, quality of the media is often lost when transmitting the media data from the in-operating room devices to the cloud server due to bandwidth restrictions. Additionally, if connection to the server is lost and/or the server otherwise fails, the information captured during the downtime will be lost in the recording. The relative latency between devices participating in the telehealth session that are located in distinct physical locations poses difficulties in synchronizing the recording to the point of data capture for each device. What is needed are improved techniques for generating high quality recordings of telehealth sessions. Further, what is needed are telehealth systems that provide improved security, privacy, reliability, and quality of service.

SUMMARY

Embodiments of the present disclosure solve the above-described problems by providing systems, methods, and computer-readable media for hybrid media distribution for telehealth sessions. Telehealth sessions may be carried out using WebRTC video conferencing between a local site (e.g., a hospital operating room) and one or more remote participants. The remote participants may connect to the telehealth session via a remote server. At the local site, local hardware may run a local server, and all devices at the local site may be connected to the local server. Media captured by the devices at the local site may be transmitted to the local server before being relayed to the remote participants. The local server may obscure portions of the data before the data leaves the local site to protect the privacy of the patient. The local server may transmit the obscured data to the remote server, and the remote server may in turn broadcast the data to the remote participants. Various aspects of the present disclosure provide a resilient architecture, which may withstand network outages, bandwidth issues, and the like while maintaining a quality telehealth session and preserving the privacy of the patient.

In some aspects, the techniques described herein relate to a system for hybrid media distribution for a telehealth session, including: a local server operating on a local network, the local server disposed in a first location associated with a patient; at least one local media device operating on the local network, the at least one local media device configured to capture media associated with the patient and transmit the media to the local server; and a local client device connected to the telehealth session; and a remote server disposed in a second location distinct from the first location, wherein the local server includes at least one local server processor configured to execute computer-executable instructions to: receive the media from the at least one local media device; obscure a portion of the media to obtain obscured media; transmit the obscured media to the remote server and to the local client device; wherein the remote server includes at least one remote server processor configured to execute computer-executable instructions to: broadcast the obscured media to at least one remote client device connected to the telehealth session.

In some aspects, the techniques described herein relate to a system, wherein the first location associated with the patient is an operating room.

In some aspects, the techniques described herein relate to a system, wherein the remote server is further configured to: receive remote media from the at least one remote client device; and transmit the remote media to the local server; and wherein the local server is further configured to: receive the remote media from the remote server; and broadcast the remote media to the local client device.

In some aspects, the techniques described herein relate to a system, wherein the at least one local media device includes at least one camera and at least one microphone.

In some aspects, the techniques described herein relate to a system, wherein the at least one local server processor is further configured to execute computer-executable instructions to record a native recording of the obscured media.

In some aspects, the techniques described herein relate to a system, wherein obscuring the media includes adding a Gaussian blur to obscure an identifying feature of the patient or other information in the environment that may compromise patient privacy.

In some aspects, the techniques described herein relate to a system, wherein the system further includes: a standby remote server configured to be provisioned responsive to a failure of the remote server.

In some aspects, the techniques described herein relate to a system for hybrid media distribution for a telehealth session, including: a local server operating on a local network, the local server disposed in a first location associated with a patient; at least one local media device configured to capture media associated with the patient and transmit the media to the local server; and a remote server communicatively coupled to the local server, wherein the local server includes at least one local server processor configured to execute computer-executable instructions to: receive the media from the at least one local media device; obscure a portion of the media to obtain obscured media; transmit the obscured media to the remote server; wherein the remote server includes at least one remote server processor configured to execute computer-executable instructions to: broadcast the obscured media to at least one remote client device connected to the telehealth session.

In some aspects, the techniques described herein relate to a system, wherein the at least one remote server processor is configured to execute additional computer-executable instructions to: responsive to receiving remote media from the at least one remote client device, transmit the remote media to the local server.

In some aspects, the techniques described herein relate to a system, wherein the at least one local server processor is configured to execute additional computer-executable instructions to: responsive to receiving the remote media from the remote server, broadcast the remote media to at least one local client device in the first location.

In some aspects, the techniques described herein relate to a system, wherein the system further includes a recording server including at least one recording server processor configured to execute computer executable instructions to: receive, from the local server, a local recording of the telehealth session; receive, from the remote server, a remote recording of the telehealth session; and generate a synchronized recording of the telehealth session based on the local recording and the remote recording.

In some aspects, the techniques described herein relate to a system, wherein the at least one recording server processor is further configured to execute computer-executable instructions to: determine a latency between the local server and the remote server, wherein generating the synchronized recording includes synchronizing the local recording and the remote recording based on the latency.

In some aspects, the techniques described herein relate to a system, wherein the local server is further configured to transmit a WebRTC simulcast of the obscured media to the remote server, and wherein the remote server is further configured to simulcast the obscured media to the at least one remote client device.

In some aspects, the techniques described herein relate to a system, further including an additional remote server configured to be provisioned responsive to a number of remote client devices connected to the remote server reaching a threshold number.

In some aspects, the techniques described herein relate to a system for hybrid media distribution for a telehealth session, including: an in-hospital network, including: a local server; a local client device connected to the local server; at least one camera for capturing video of an operation associated with the telehealth session; and at least one microphone for capturing audio associated with the telehealth session; and a plurality of remote servers communicatively coupled to the local server, wherein the local server includes at least one local server processor configured to execute computer-executable instructions to: receive the video from the at least one camera and the audio from the at least one microphone; and transmit the video and the audio to the plurality of remote servers; and wherein each of the plurality of remote servers includes at least one remote server processor configured to execute computer-executable instructions to: receive the video and the audio from the local server; and broadcast the video and the audio to one or more remote client devices.

In some aspects, the techniques described herein relate to a system, wherein the at least one local server processor includes additional computer-executable instructions to: prior to transmitting the video to the plurality of remote servers, obscuring at least a portion of the video.

In some aspects, the techniques described herein relate to a system, wherein the local client device is configured to receive user input defining the portion of the video to obscure.

In some aspects, the techniques described herein relate to a system, wherein the plurality of remote servers includes at least one edge server.

In some aspects, the techniques described herein relate to a system, wherein the at least one local server processor includes additional computer-executable instructions to: save a native copy of the video and the audio in a network attached storage.

In some aspects, the techniques described herein relate to a system, further including: a recording server including at least one recording server processor configured to execute computer-executable instructions to: receive a local recording from the local server and a remote recording from a remote server of the plurality of remote servers; and generate a composite recording of the telehealth session by comparing a frame from the local recording with a corresponding frame from the remote recording; and replace the corresponding frame from the remote recording with the frame from the local recording upon determining that the frame is associated with at least one of a higher resolution or a higher frame rate than the corresponding frame.

In some aspects, the techniques described herein relate to a hybrid media distribution system for a telehealth session, including: a local server operating on a local network, the local server located in a location associated with a patient; at least one local client device connected to the local network; at least one local media device connected to the local network, wherein the at least one local media device is configured to capture media of the telehealth session in the location associated with the patient; and at least one remote server operating on a remote network; wherein the local server includes at least one local server processor configured to execute computer-executable instructions to: receive the media from the at least one local media device; obscure at least a portion of the media to obtain obscured media; and broadcast the obscured media to the at least one remote server; and wherein the at least one remote server includes at least one remote server processor configured to execute computer-executable instructions to: receive the obscured media from the local network; and responsive to receiving the obscured media, broadcast the obscured media to at least one remote participant.

In some aspects, the techniques described herein relate to a hybrid media distribution system, wherein the at least one remote server includes at least one remote standby server, wherein the at least one remote standby server is a failover server for the telehealth session.

In some aspects, the techniques described herein relate to a hybrid media distribution system, further including: a local storage operating on the local network, wherein the local storage stores a native recording of the obscured media.

In some aspects, the techniques described herein relate to a hybrid media distribution system, further including: at least one remote storage operating on the remote network, wherein the at least one remote storage stores remote recording of the telehealth session, and wherein the local server is further configured to combine the native recording and the remote recording to generate a combined recording of the telehealth session.

In some aspects, the techniques described herein relate to a hybrid media distribution system, wherein transmitting the obscured media includes adaptively streaming the obscured media to the at least one remote server based on a network quality associated with the telehealth session.

In some aspects, the techniques described herein relate to a hybrid media distribution system, wherein adaptively streaming the obscured media includes prioritizing degradations in a frame rate of the telehealth session over degradations in a bandwidth or a resolution of the telehealth session.

In some aspects, the techniques described herein relate to a hybrid media distribution system, wherein the at least one remote server includes a first remote server and a second remote server, the first remote server disposed in a first geographic location distinct from a second geographic location of the second remote server.

In some aspects, the techniques described herein relate to one or more non-transitory computer-readable media storing computer-executable instructions that, when executed by at least one processor, perform a method of hybrid media distribution for telehealth sessions, including: receiving, at a local server, media data for a telehealth session from at least one local media device connected to the local server, wherein the local server is disposed in a first location associated with a patient; obscuring, at the local server, the media data to obtain obscured media; transmitting, by the local server, the obscured media to a first remote server, a second remote server, and at least one local client device connected to the local server, wherein the second remote server is a standby server for the first remote server; and responsive to receiving the obscured media at the first remote server, broadcasting the obscured media to one or more remote participants connected to the first remote server.

In some aspects, the techniques described herein relate to a media, further including: responsive to an outage in the first remote server, transitioning the one or more remote participants to the second remote server.

In some aspects, the techniques described herein relate to a media, further including: receiving, at the first remote server, remote media from a participant of the one or more remote participants; transmitting the remote media from the first remote server to the local server; and broadcasting the remote media from the local server to at least one local client device connected to the local server.

In some aspects, the techniques described herein relate to a media, wherein the first remote server is configured to simulcast the obscured media to the one or more remote participants.

In some aspects, the techniques described herein relate to a media, further including: responsive to detecting a first change in a quality of a connection between the local server and the first remote server, reducing a frame rate of the obscured media; and responsive to detecting a second change in the quality of the connection and detecting that the frame rate of the obscured media is reduced to a predefined frame rate threshold, reducing at least one of a bit rate or a resolution of the obscured media.

In some aspects, the techniques described herein relate to a media, further including: responsive to detecting a threshold number of the one or more remote participants connected to the first remote server, provisioning a third remote server for incoming remote participants; and transmitting the obscured media to both the first remote server and the third remote server.

In some aspects, the techniques described herein relate to a method for hybrid media distribution for a telehealth session, including: receiving, at a local server operating on a hospital network, local media data of an operation being performed on a patient within a hospital associated with the hospital network; applying at least one obscuration to the local media data to obtain obscured media; transmitting the obscured media to a plurality of remote servers; responsive to receiving the obscured media at each of the plurality of remote servers, broadcasting, by at least a subset of the plurality of remote servers, the obscured media to a respective plurality of remote participants.

In some aspects, the techniques described herein relate to a method, wherein the local server is configured to adaptively stream the obscured media to the plurality of remote servers, and wherein the subset of the plurality of remote servers is configured to simulcast the obscured media to the respective plurality of remote participants.

In some aspects, the techniques described herein relate to a method, wherein the local server is configured to generate a local recording of the telehealth session, and wherein each of the plurality of remote servers is configured to generate a remote recording of the telehealth session.

In some aspects, the techniques described herein relate to a method, further including: generating a combined recording using the local recording and the remote recording generated at each of the plurality of remote servers, wherein generating the combined recording includes determining that a frame transmitted from the local server to the plurality of remote servers did not arrive at a remote server, and replacing the frame with a corresponding frame from another remote server of the plurality of remote servers in the combined recording.

In some aspects, the techniques described herein relate to a method, wherein generating the combined recording further includes synchronizing the local recording and the remote recording based on a latency between the local server and each of the subset of the plurality of remote servers.

In some aspects, the techniques described herein relate to a method, further including: receiving, from a session host user, an instruction defining at least of a portion the local media data to apply the at least one obscuration.

In some aspects, the techniques described herein relate to a method, wherein at least one remote server of the plurality of remote servers is a standby server.

In some embodiments, the techniques described herein relate to a hybrid media distribution system for a telehealth session, including: a local server operating on a local network, the local server disposed in a location associated with a patient; at least one local media device connected to the local network and configured to capture local media of the telehealth session; and at least one remote server operating on a remote network; wherein the local server includes at least one local server processor configured to execute computer-executable instructions to: receive the local media from the at least one local media device; broadcast the local media to the at least one remote server; and generate a first recording including the local media captured by the at least one local media device; and wherein the at least one remote server includes at least one remote server processor configured to execute further computer-executable instructions to: receive the local media from the local network; broadcast the local media to at least one remote participant; generate a second recording including data received from the at least one remote participant; log a first plurality of latencies between the local server and the at least one remote server; log a second plurality of latencies between the at least one remote server and the at least one remote participant; and generate a synchronized recording of the telehealth session based on the first recording, the second recording, the first plurality of latencies, and the second plurality of latencies.

In some embodiments, the techniques described herein relate to a hybrid media distribution system, wherein logging the first plurality of latencies includes determining each latency of the first plurality of latencies based on a data packet sent between the local server and the at least one remote server.

In some embodiments, the techniques described herein relate to a hybrid media distribution system, wherein the at least one local server processor is further configured to: apply at least one obscuration to the local media prior to transmitting the local media to the at least one remote server.

In some embodiments, the techniques described herein relate to a hybrid media distribution system, wherein each of the first plurality of latencies is a combined latency including a network latency between the local server and the at least one remote server and a computational latency associated with applying the at least one obscuration to the local media.

In some embodiments, the techniques described herein relate to a hybrid media distribution system, wherein the first plurality of latencies comprises a plurality of video latencies associated with video data transmitted from the local server to the remote server and a plurality of audio latencies associated with audio data transmitted from the local server to the remote server.

In some embodiments, the techniques described herein relate to a hybrid media distribution system, wherein the at least one local media device includes a telesurgery device, and wherein the at least one remote participant remotely operates the telesurgery device.

In some embodiments, the techniques described herein relate to a hybrid media distribution system, wherein at least one of the local server or the at least one remote server is further configured to: restrict control of the remote operation of the telesurgery device in response to an increase in the second plurality of latencies.

In some embodiments, the techniques described herein relate to one or more non-transitory computer-readable media storing computer-executable instructions that, when executed by at least one processor, perform a method of hybrid media distribution for telehealth sessions, including: receiving, at a local server, local media data of a telehealth session from at least one local media device connected to the local server, wherein the local server is disposed in a first location associated with a patient; transmitting, by the local server, the local media data to at least one remote server operating on a remote network; generating a native recording of the local media data on the local server responsive to receiving the local media data at the at least one remote server, broadcasting the local media data to one or more remote participants connected to the at least one remote server; receiving, at the at least one remote server, remote media from a remote participant from the one or more remote participants; generating a remote recording of the remote media on the at least one remote server; logging a first plurality of latencies between the local server and the at least one remote server; logging a second plurality of latencies between the at least one remote server and the one or more remote participants; and generating a synchronized recording of the telehealth session based on the native recording, the remote recording, the first plurality of latencies, and the second plurality of latencies.

In some embodiments, the techniques described herein relate to a media, further including: transmitting the remote media from the at least one remote server to the local server; and broadcasting the remote media from the local server to at least one local client device connected to the local server.

In some embodiments, the techniques described herein relate to a media, wherein generating the synchronized recording includes adjusting a video feed associated with the remote recording based on the second plurality of latencies.

In some embodiments, the techniques described herein relate to a media, further including: detecting an increase in the second plurality of latencies; transmitting, by the local server, a notification indicative of the increase in the second plurality of latencies to the one or more remote participants.

In some embodiments, the techniques described herein relate to a media, further including: prior to transmitting the local media data to the at least one remote server, applying, by the local server, an obscuration to at least a portion of the local media data.

In some embodiments, the techniques described herein relate to a media, further including: logging a plurality of computational latencies; and responsive to detecting an increase in the plurality of computational latencies, changing an obscuring method for obscuring the portion of the local media data.

In some embodiments, the techniques described herein relate to a method for hybrid media distribution for a telehealth session, including: receiving, at a local server operating on a hospital network, local media data of an operation being performed on a patient within a hospital associated with the hospital network; transmitting the local media data to a remote server; responsive to receiving the local media data at the remote server, broadcasting, by the remote server, the local media data to a remote participant; generating, on the local server, a first recording including the local media data; receiving remote media data from the remote participant at the remote server; transmitting the remote media data to the local server; generating, on the remote server, a second recording including the remote media data; and generating a combined recording of the telehealth session based on the first recording and the second recording; and synchronizing the combined recording by adjusting at least one of the first recording or the second recording based on a plurality of network latencies logged during the telehealth session.

In some embodiments, the techniques described herein relate to a method, wherein the first recording includes a first frame rate higher than a second frame rate of the second recording.

In some embodiments, the techniques described herein relate to a method, wherein synchronizing the combined recording further includes repeating frames from the second recording such that the second frame rate is increased to be equal to the first frame rate.

In some embodiments, the techniques described herein relate to a method, further including: prior to transmitting the local media data to the remote server, applying, by the local server, an obscuration to the local media data.

In some embodiments, the techniques described herein relate to a method, further including: generating a third recording including video data captured by a telesurgery device, logging a third plurality of latencies associated with a plurality of log messages generated by the telesurgery device and transmitted to the local server, wherein the combined recording further includes the third recording, and wherein synchronizing the combined recording is further based on the third plurality of latencies.

In some embodiments, the techniques described herein relate to a method, wherein the local media data includes at least one of audio data, video data, telestation data, telemetry data, or telesurgery data.

In some embodiments, the techniques described herein relate to a method, wherein at least one of the local server or the remote server is configured to take a correct action in response to an increase in a latency associated with the telesurgery data.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein:

FIG. 4 depicts a flowchart illustrating operation of the hybrid media distribution system for some embodiments;

Figure 1:
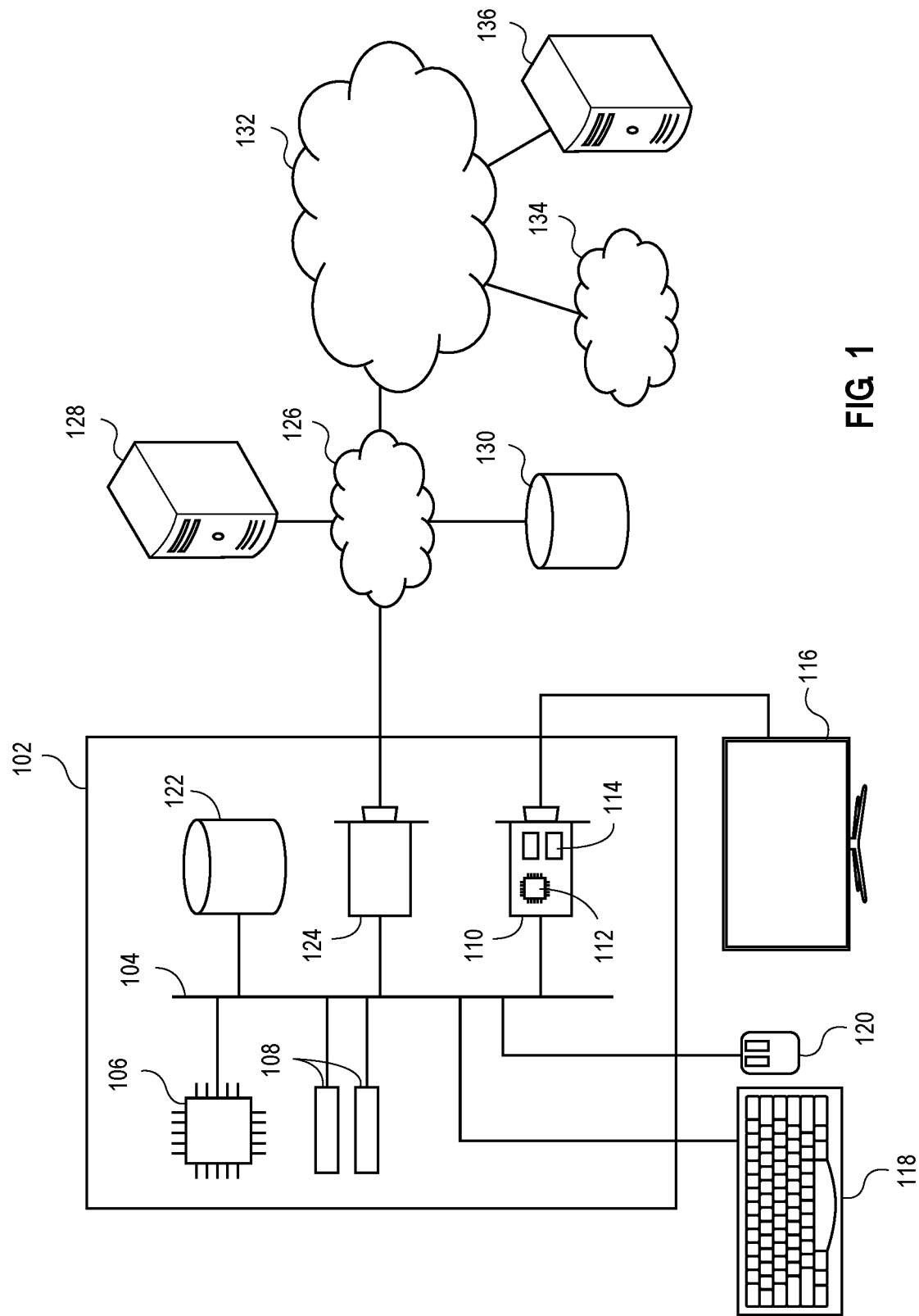
FIG. 1 depicts an exemplary hardware platform relating to some embodiments.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The following detailed description references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Turning to FIG. 1, an exemplary hardware platform for certain embodiments is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple buses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media and may be internally installed in computer 102 or externally and removably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently and may be non-transitory computer-readable media storing data or computer-executable instructions. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth®, or Wi-Fi (i.e., the IEEE 102.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex API (such as, for example, Structured Query Language), a simple API providing only read, write, and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

System Overview

Embodiments described herein are generally directed to systems, methods, and computer-readable media for hybrid media distribution for telehealth sessions. The telehealth session may be conducted using WebRTC or any other real-time communications protocol. Participants may join the telehealth session remotely by connecting to a remote server. A local server may run on hardware in the location where the medical operation is taking place, such as in a hospital operating room, or elsewhere within the hospital. The local server may operate on a local network, such as a hospital network that is not otherwise connected to the Internet. On-site devices (e.g., client computing devices, cameras, etc.) may be connected to the local server and transmit data to the local server via the local network. The local server may adjust the media from the on-site devices before transmitting the media to the remote server. For example, the local server may apply a blur effect to obscure an identifying feature of the patient being operated on to protect the privacy of the patient. Once the remote server receives the adjusted media from the local server, the remote server may broadcast the adjusted media to the remote participants as part of the telehealth session. In some embodiments, the telehealth session may be recorded. The local server and the remote server may make separate recordings that may be synchronized and combined to generate a composite recording. Latencies may be monitored for devices in the telehealth session, which may be used to synchronize the recording.

Figure 2A:
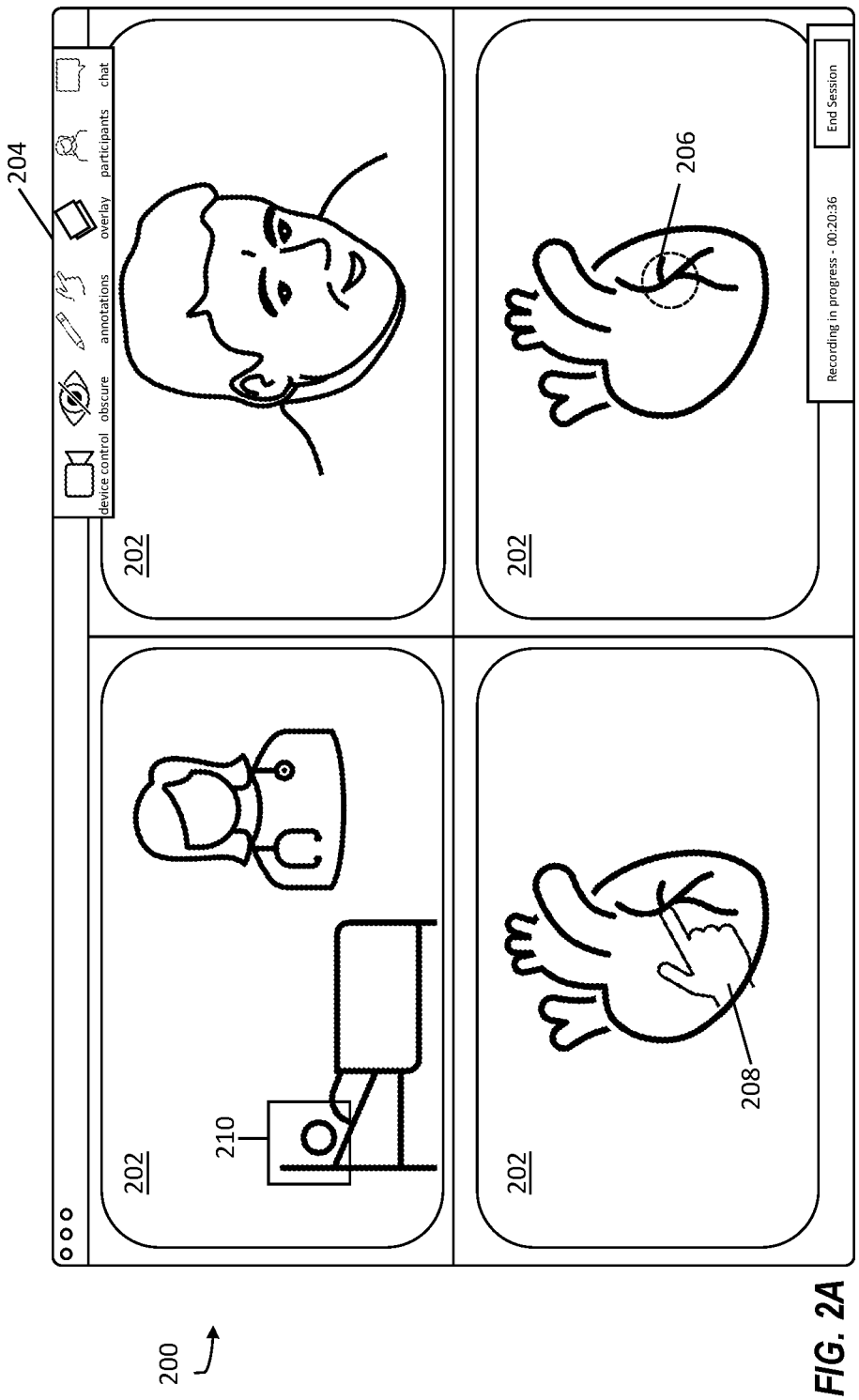
FIG. 2A depicts an exemplary user interface relating to some embodiments.

FIG. 2A depicts an exemplary user interface 200 illustrating a video stream in the context of a telehealth session, which will be useful in understanding embodiments discussed herein. User interface 200 may include a plurality of video windows 202. Each video window 202 may be associated with a separate video stream. For example, as shown, for a telesurgery, a first video window (top left) may display an in-operating room video stream of the patient and medical practitioners performing the operation, a second video window (top right) may display a video stream of a remote participant, a third video window (bottom left) may show medical imagery of the patient being operated on, and a fourth video window may display an annotated view of the medical imagery. As discussed further below, in some embodiments, participants may annotate over portions of the video stream to assist with the telesurgery. Various other configurations of user interface 200 are within the scope hereof. In some embodiments, video windows 202 may display auxiliary information, such as a presentation that includes instructions for performing the surgery. As yet another example, a video window 202 may display data associated with the telesurgery, such as real-time vital information of the patient. Generally, the video windows may display any data stream. While four video windows 202 are illustrated, it will be appreciated that user interface 200 may comprise fewer or more than four video windows 202.

User interface 200 may comprise a toolbar 204 comprising various tools allowing a participant to participate in the telehealth session. In some embodiments, toolbar 204 comprises a chat affordance that may be actuated to cause display of a chat window (not shown) for the telehealth session. In some embodiments, a single chat window is provided for all participants. In some embodiments, participants can chat via direct messages or multiple person direct messages. In some embodiments, toolbar 204 comprises a "participants" affordance that may be actuated to view the participants of the telehealth session. Participants may be shown with status indicators, such as an indicator that the participant is using an annotation tool and an indicator that the participant is transmitting audio.

In some embodiments, toolbar 204 comprises an overlay tool for overlaying content onto a video window 202. For example, if the telesurgery is for operating on a patient's bone, x-ray imagery of the bone may be overlaid on the live video feed of the surgeon operating on the bone. In some embodiments, toolbar 204 comprises an annotation tool for annotating over the telehealth session. When actuated, the annotation tool may allow for a participant to annotate over video displayed in a video window 202. In some embodiments, annotations 206 can be made by a participant drawing over the video. For example, a participant may use an input device (e.g., mouse, stylus, etc.) to draw on a video window 202. In some embodiments, preconfigured annotations are provided, such as preset shapes (e.g., rectangles, circles), that can be added as annotations 206 to the video stream. Annotations may be customized, such as by choosing an annotation color, adjusting a line width of the annotation, a transparency level, or the like. In some embodiments, annotations 206 are inserted using a HTML canvas over the video stream on which annotations 206 can be written. Other markup languages may be used for inserting annotations 206 over a video stream in the telehealth session.

Along with overlaying imagery and obscuring media (discussed further below), other preprocessing may be applied to the media before the media is broadcasted to the remote participants. For example, artificial intelligence techniques may be used to enhance or otherwise adjust the displayed imagery. For example, if medical imagery of the patient's tissue is being streamed, AI techniques may be used to artificially change the color of the tissue to help remote participants to better distinguish between the tissue layers. Various other preprocessing techniques may be used to enhance the video and/or audio transmitted as part of the video. For example, audio super resolution and/or video super resolution techniques may be used to upscale transmitted audio and video for the telehealth session.

In some embodiments, annotations 206 can be created via augmented reality (AR) techniques. In some embodiments, an AR hand 208 is provided for annotating the video. In some embodiments, the AR hand 208 is a superimposed image of a participant's hand captured by a camera. The movement of the participant's hands may be reflected in the video, and the participant can add annotations 206 to the video via the hand movements. For example, annotations 206 may be created to call out or otherwise indicate important regions of a video. As depicted, a remote participant has drawn an annotation 206 over a portion of the heart. For example, the annotation 206 could be used to indicate an abnormality in the imagery, where to make an incision, and the like. The use of AR annotations allows for free-form annotations to be made as the remote participant can simply move their hand to make the annotation 206. In some embodiments, as shown in FIG. 2A, one video window 202 displays the video stream with annotations 206 overlaid, while a second video window 202 displays the unannotated video.

In some embodiments, the camera for AR hand 208 can capture imagery of the participant manipulating a tool, such as a surgical instrument, to mimic the procedure to be performed locally, and this video data may be captured and overlaid onto the video as an annotation 206. Thus, in some embodiments, annotations may be dynamic. Other augmented reality techniques, such as the use of an augmented reality glove, or the like, are within the scope hereof. Other techniques for augmented reality annotations are discussed in U.S. Pat. No. 9,576,106, entitled "REMOTE INSTRUCTION AND MONITORING OF HEALTH CARE", the entirety of which is incorporated by reference.

Toolbar 204 may further comprise an obscure tool to indicate which regions of the video should be obscured. As previously discussed, portions of the media may need to be obscured to preserve the privacy of the patient. In some embodiments, the obscure tool may be used to define an obscure region 210 that is to be obscured before being transmitted to the other participants of the telehealth session. For example, an obscure region 210 may be defined over a region of video window 202 where the patient's face is located, and a Gaussian blur may be applied to obscure region 210 to blur the patient's face. Because the patient will generally be stationary during the operation, the obscure region 210 to be obscured may be static during the telehealth session. However, various techniques may be used to track the identified regions during the telehealth session to ensure that the regions are obscured if they move relative to the video window 202. For example, facial tracking may be used to track the patient's face during the telehealth session, and if the patient's face moves, the obscure region 210 may be adjusted accordingly. A user may add, delete, and modify obscure region 210 during the telehealth session.

In some embodiments, audio data may also be obscured. For example, audio data may be obscured by replacing the data with other audio, such as bleeping over an utterance of the patient's name, by removing the portion of the audio data from transmission, or by any other method. By obscuring data originating from the operating room before the data leaves the operating room and is transmitted to the cloud, the privacy of the patient may be preserved before the media data leaves the operating room.

In some embodiments, toolbar 204 further comprises a device control tool. In some embodiments, the device control tool allows for participants to control a camera operating in the operating room remotely. For example, an in-operating room (in-OR) camera may have pan, tilt, zoom functionality, which may be controlled remotely by a remote participant via the device control tool. For example, a remote participant may be instructing a local surgeon on how to perform a medical procedure. The local surgeon may have arranged one or more in-OR cameras around the operating room to capture video while the local surgeon is performing the operation. The remote participant can adjust the positioning of the camera as needed without requiring the local surgeon to physically adjust the camera, which may be difficult while the local surgeon is performing the surgery. In some embodiments, the device control tool can be used to adjust a zoom level of the camera, how the video is displayed (e.g., changing contrast level), and the like.

The device control tool may also provide control of other in-OR media devices by the remote participant. For example, the remote participant may be able to turn in-OR microphones on or off. As another example, within the OR, a display is often positioned such that the local surgeons can view the telehealth session while performing the medical procedure. The display may be placed on a movable cart or other device for positioning the display. Accordingly, in some embodiments, it is contemplated that the device control tool may enable a participant to adjust a position of the display. For example, the participant may adjust the position of the display to provide the local surgeons a better view of the display without the surgeons needing to pause the procedure to adjust the display themselves.

In some embodiments, a participant of the telehealth session operates as a session host. The session host may have control over various settings for the telehealth session. For example, the session host may initialize the telehealth session and may invite participants to join the telehealth session. As another example, the session host may configure user interface 200, such as which information is displayed during the telehealth session. In some embodiments, each end user may configure the layout of user interface 200 such that each end user may be presented a different user interface. In some embodiments, the session host can configure the layout of user interface 200, such as maximizing the display of a video window 202 within user interface 200 before or during the telehealth session. The session host may also configure controls on whether remote participants can transmit audio, video, chat, telestration (e.g., annotations), or any combination thereof as part of the telehealth session.

In some embodiments, remote participants may be restricted from transmitting audio/video data such that the remote participants only participate via annotations and/or chat. In some embodiments, the session host is the only participant that can indicate regions of the video to be obscured. In some embodiments, the session host can designate one or more other participants to input obscure region 210. In some embodiments, the session host is a user operating a computer connected to the local network associated with the operating room, as discussed further below.

Figure 2B:
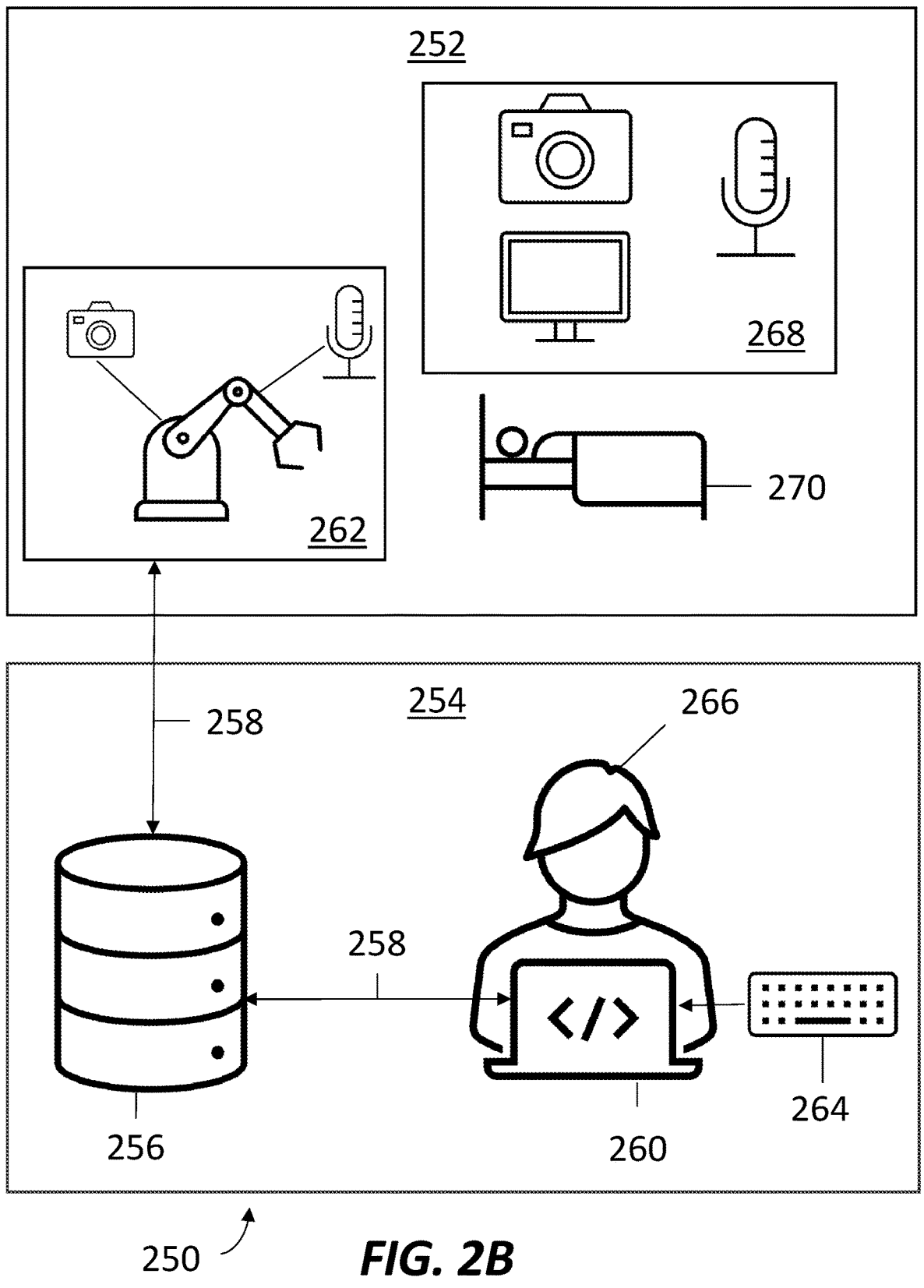
FIG. 2B schematically depicts an exemplary hospital configured for telesurgery for some embodiments.

FIG. 2B schematically depicts an exemplary hospital 250 configured for telesurgery, which will be useful in understanding embodiments discussed herein. In some embodiments, hospital 250 comprises a patient operating room 252 and one or more secondary rooms 254. In some embodiments, the patient operating room 252 and the secondary room 254 are physically different rooms within the hospital 250. The patient operating room 252 may be the room in which the telehealth operation (e.g., surgery) is taking place, while the secondary room 254 may be a lab room or the like that is within the hospital 250 but is separate from the patient operating room 252. Persons in the secondary room 254 may be participating in the telehealth operation without being physically present in the patient operating room 252. For example, the secondary room 254 may be a pathology lab performing tests on tissue removed from the patient being operated on in patient operating room 252.

In some embodiments, the hospital 250 comprises a local server 256 operating on a local network 258. The local server 256 may be located in patient operating room 252, secondary room 254, or elsewhere within the hospital 250. Client devices 260 and telesurgery devices 262 may transmit data (e.g., audio/video data, control signals, sensor data, etc.) to the local server 256 via local network 258. While client device 260 is shown in secondary room 254, it will be appreciated that a client device 260 may likewise be located in patient operating room 252, e.g., a surgeon may view the telehealth session on a client device 260 while performing the surgery. In some embodiments, all network devices in hospital 250 that are participating in the telehealth session are connected to local server 256 via local network 258. As discussed in further detail below, local server 256 may allow for local data of the telehealth session captured in hospital 250 to be processed (e.g., modified to protect patient privacy) prior to the data being transmitted out of local network 258 where the data may be accessible by persons not authorized to view private information related to the telehealth session. It is one advantage of the present disclosure that by connecting all devices within hospital 250 to local server 256 such that the in-hospital devices do not need to connect to a remote server, bandwidth savings can be realized. Further, each device may have substantially the same latency to local server 256 due to local server 256 being physically located in hospital 250, which may reduce the computational cost of synchronizing a telehealth session recording based on latencies tracked for each device.

In some embodiments, client device 260 is a smartphone, laptop, desktop computer, or any other computing device discussed above with respect to FIG. 1. In some embodiments, client device 260 may comprise peripherals such as cameras, microphones, and input devices 264 to capture media and input from client user 266. Generally, the cameras or microphones may be any form of camera (e.g., a web camera) and may be connected to client device 260 wired or wirelessly. Input devices 264 may comprise a keyboard, mouse, controller, or any other input peripheral for a user 266 to provide input to client device 260. In some embodiments, a user 266 operating client device 260 may control one or more telesurgery devices 262 located in patient operating room 252 using input devices 264. Accordingly, in some embodiments, local server 256 may be configured to transmit instructions received from client device 260 to telesurgery device 262 to control operations thereof. For example, if telesurgery device 262 is a robotic scalpel, input device 264 may be a controller that allows the client user 266 to direct the movement of the robotic scalpel.

Telesurgery devices 262 may include surgical equipment, such as robotic surgery devices, that may be used during the telesurgery and generate data. In some embodiments, telesurgery devices 262 may comprise cameras, microphones, or any other device configured to capture media or other sensor data relating to the operation of the telesurgery devices 262. For example, telesurgery devices 262 may include a surgical tool, such as a scalpel, a drill, a suction machine, or any other surgical device. In some embodiments, cameras or microphones may be coupled directly to or integrated with the surgical tool. This coupling allows media transmitted from cameras to show precise images of the operation from the surgical tool, for example. In some embodiments, the surgical tool may be configured to capture haptic data or other sensor data. For example, if the surgical tool is a drill, the drill may capture haptic data that reflects physical feedback on the drill. This haptic data may be transmitted from the telesurgery device 262 to the client device 260 through the local server 256. In some embodiments, telesurgery device 262 may be autonomous or semi-autonomous.

In some embodiments, hospital 250 further comprises local media devices 270. Local media devices 270 may comprise cameras, microphones, or any other device configured to capture media of the telehealth operation. For example, local media devices may include smart glasses worn by the surgeon that captures and transmits video of the surgery to capture a first-person perspective of the surgery. Generally, the cameras may be any form of camera and may transmit data to local server 256 wired or wirelessly. In some embodiments, local media devices 270 may capture media of a patient 272 independent of telesurgery devices 262. In some embodiments, microphones may be placed around the operating room 252 to capture audio of the telehealth session. In some embodiments, local media devices 270 includes a display monitor located in patient operating room 252 for persons in patient operating room 252 to view and/or participate in the telehealth session.

Local server 256 may comprise a message broker (see FIG. 3A) for managing communications between devices 260, 262, 268 during the telehealth session. The message broker may utilize a publication-subscription architecture and may be, for example, MQTT 5.0. In some embodiments, each device 260, 262, 20 participating in a telehealth session registers with the telehealth session provider prior to the telehealth session. The registration may comprise each device 260, 262, 268 undergoing a security protocol to authenticate the device. In some embodiments, each device 260, 262, 268 may be required to have requisite security credentials to join a specific telehealth session. Accordingly, once registered, the devices 260, 262, 268 may communicate with one another and exchange data with the privacy of the exchanged data being guaranteed. Furthermore, by registering with the telehealth session provider, the device data can be associated with the device within the telehealth session. For example, if a telesurgery device 262 captures and transmits video during a surgical operation, the video can be linked to the device based on the pre-registration of the device. For example, the robotic device video may be displayed in a video window 202 and labeled "Video from Robotic Device 1."

The message broker may also be used to determine latency for devices 260, 262, 268 during the telehealth session, which may be used to generate a synchronized recording of the telehealth session, as discussed in further detail hereinafter. In some embodiments, messages sent between the message broker and devices 260, 262, 268 comprise timestamps that may be used to determine a latency therebetween. In some embodiments, the message broker and/or a device 260, 262, 268 sends a message that is configured to be sent round trip such that the initial send time and the return time can be used to determine the latency between the message broker and the sending device 260, 262, 268. The message may be a data packet configured only for measuring latency, or the message may include data related to the telehealth session (e.g., sensor data from a biometric device) having a timestamp from which the latency can be determined. For example, the message may be a log message from a biometric sensor that includes sensor data along with a timestamp, and the timestamp may be used to determine latency. For example, the biometric sensor may communicate the log message to local server 256 along with the timestamp indicating when the log message was transmitted, local server 256 may transmit the log message back to the biometric sensor, and the biometric sensor may compare the time at which the log message was returned to the timestamp to determine the latency to local server 256. In some embodiments, local server 256 determines the latency based on the timestamp and the time at which the log message was received at local server 256. In some embodiments, prior to the telehealth session beginning, device clocks may be synchronized to accurately determine latency based on timestamps. In some embodiments, the message broker periodically (e.g., at regular or irregular intervals) broadcasts a message to all or a subset of connected devices 260, 262, 268 that is returned and used to determine the latency from the message broker (running on local server 256) to each device 260, 262, 268. In some embodiments, WebRTC statistics, jitter buffers, and the like may also be used to determine latency for devices 260, 262, 268.

By tracking latency for devices 260, 262, 268 a recording of the telehealth session can be generated that is synchronized to the point of data capture for each device. For example, if a telesurgery device 262 has a camera that captures video that is transmitted to local server 256 with 5 ms latency, the video may be time shifted by 5 ms when the recording is generated. Thus, if the telesurgery device 262 is also measuring sensor data, the captured video may be synchronized to the measured sensor data. Generating such a synchronized recording may be useful when reviewing a telehealth session operation, where it may be critical to have the video data exactly aligned with the sensor data because of the critical events that may happen with the period of latency between capturing and transmitting the video data and the logging of sensor data, for example.

It will be appreciated that various other types of latency besides latency for a video feed may be tracked, logged, monitored, or any combination thereof without departing from the scope hereof, and these latencies may similarly be used to adjust various parts of the telehealth session. For example, latency of audio data transmitted during the telehealth session may be tracked and used during and/or after the telehealth session to make adjustments to the telehealth session. Similarly to synchronizing video feeds based on latency, audio feeds may be synchronized when generating recordings of the telehealth session. Tracking latency for audio during the telehealth session may also be used for making other adjustments to the audio, such as for synthesizing the audio data, or performing any other processing to the audio data. For example, when generating the composite recording, it may be desired to adjust the volume of an audio stream, such as the audio of the surgeon performing the surgery.

As discussed herein, generally, latency can be tracked for any device that is transmitting data as part of the telehealth session. Other examples of data that may have latency tracked/monitored/etc. include, but are not limited to: latency for sensor readings (e.g., to be transmitted from a surgical device to local server 256); input latency (e.g., for remotely controlling a surgical tool); ping latency; and computational latency (e.g., for applying an obscuration to the video). One of skill in the art will appreciate various other data that may be transmitted during the telehealth session and the latency for said data may be tracked and used to adjust the recording and/or for logging purposes to review after a telehealth session.

As discussed further below, in some embodiments, latency is assumed to be symmetric. That is, the latency between two devices (e.g., between local server 256 and a remote server, between a telesurgery device 262 and local server 256, etc.) is assumed to be the same when sending data from the first device to the second device. For example, the latency between local server 256 and remote server (as discussed further below) may be calculated by sending a round trip data packet between the two servers, and halving the time it takes for the data packet to return to the sender. However, in some embodiments, determining the latency is based on an assumption that the latency between two devices is asymmetrical. Thus, using the above example, a first latency may be determined for the time it takes for the data packet to be sent from the local server to the remote server may be determined, and a second latency may be determined for the time it takes the data packet to be sent from the remote server to the local server. The latency monitoring of a telehealth session may monitor latency using both symmetric latency calculations and asymmetric latency calculations. For example, for devices where it is more critical to track the latency (e.g., remotely controlled surgical devices), asymmetric latency may be assumed to ensure greater accuracy, while latency between less critical components may be assumed symmetric to save processing power in calculating the latencies.

Monitoring the latency may further be used to prevent unsafe operations of a telesurgery device 262. In some embodiments, if the local server 256 detects a latency above a threshold between for telesurgery devices 262, local server 256 may broadcast a notification to the controlling client device 260 indicative of the high latency. In some embodiments, if the local server 256 detects the latency exceeding the threshold between the telesurgery devices 262 and client device 260, local server 256 may limit the control of telesurgery devices 262 by the controlling user. For example, if telesurgery device 262 is a robotic scalpel, local server 256 may prevent a user from directing the scalpel to make an incision for a time during high network latency. As previously discussed, it is contemplated that each device in the telehealth session may monitor the device's own latency and, accordingly, broadcast to one or more other devices or servers that the device is experiencing aberrant latency. Remote control of telesurgery devices 262 may likewise be limited for remote participants of the telehealth session, as discussed in further detail below.

Hybrid Media Distribution

Figure 3A:
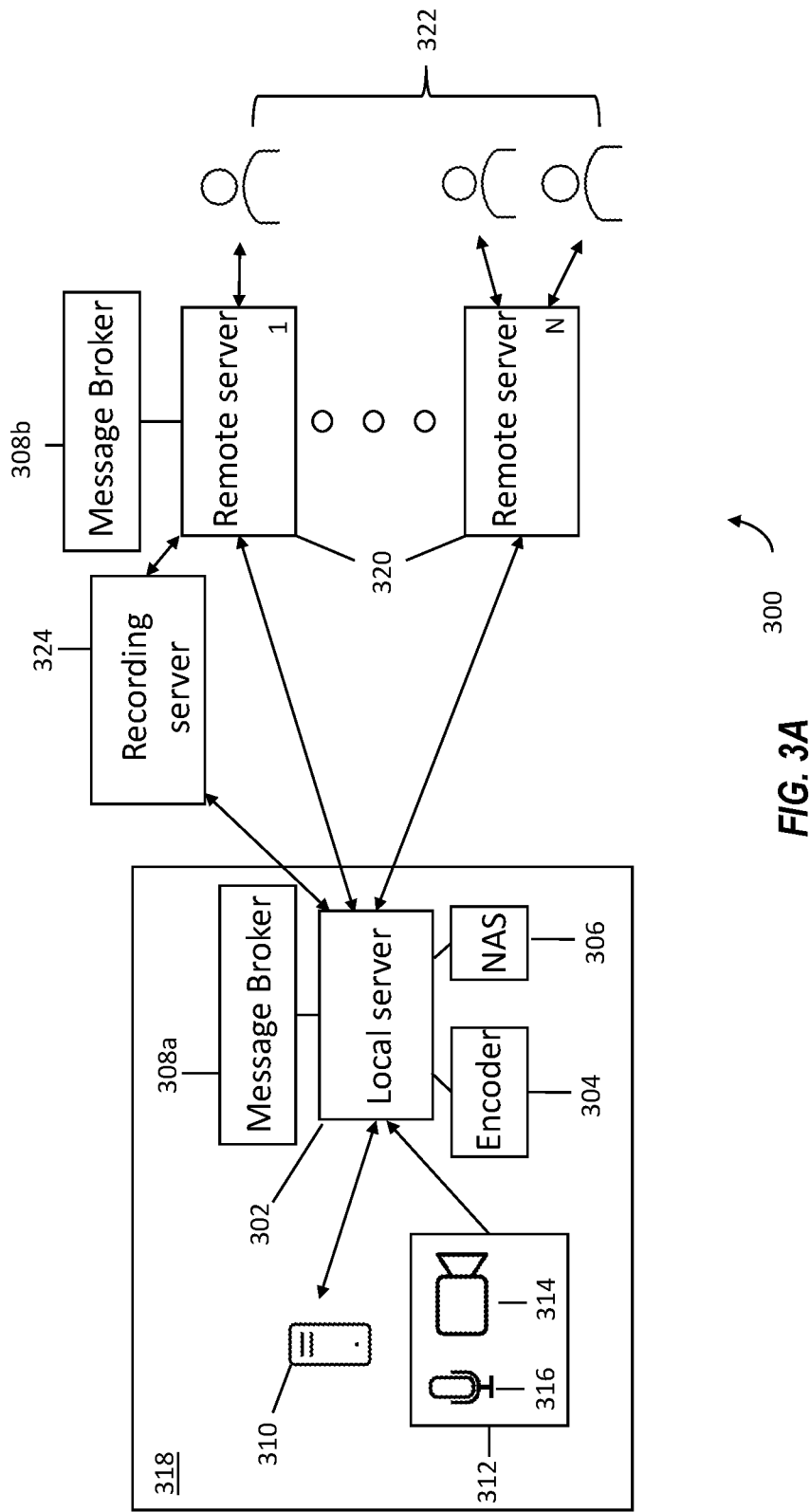
FIG. 3A depicts a hybrid media distribution system for some embodiments.

FIG. 3A illustrates a system 300 in accordance with embodiments of the present disclosure. In some embodiments, system 300 facilitates hybrid media distribution for a telehealth session that protects the privacy of the patient involved in the telehealth session. System 300 may also provide resiliency against network outages, reduced latency, and improvements in security and recordings of telehealth sessions as discussed further herein.

In some embodiments, system 300 comprises a local server 302 that comprises or is otherwise associated with an encoder 304, a network attached storage (NAS) 306, a local message broker 308a, or any combination thereof. In some embodiments, local server 302 may be local server 256 described above. A local client device 310 and local media devices 312 may transmit media data to the local server 302. In some embodiments, local media devices 312 comprise cameras 314, microphones 316, or any other device configured to obtain data associated with a medical procedure. For example, local media devices 312 may comprise medical equipment configured to take sensor readings associated with the operation. The local server 302, local client device 310, and local media devices 312 may be connected via a local network 318. Media received from local devices 310, 312 by local server 302 may be transmitted to a remote server 320. Remote server 320 may broadcast the media to remote client devices 322. Local server 302 and remote server 320 may be communicatively coupled to a recording server 324 for generating recordings of the telehealth session, as discussed further below.

In some embodiments, local server 302 is a WebRTC server configured for live video conferencing. In some embodiments, local server 302 is a JANUS® WebRTC server. In some embodiments, local server 302 runs locally on hardware located within local network 318. For example, local network 318 may be a WLAN hospital network, and local server 302 may run on hardware disposed in an operating room, or elsewhere within the hospital. Local server 302 may transmit data received from local devices 310, 312 to the remote servers 320.

Data transmitted during the telehealth session may include audio data, video data, chat data, telestration data, telesurgery data, telemetry data or any combination thereof. In some embodiments, video data is transmitted on a first channel, audio transmitted on a second channel, and chat/telestration data are transmitted together on a third channel. In some embodiments, each video stream is transmitted as a separate video stream. For example, if local client device 310 and camera 314 are both streaming video, local server 302 may forward each video stream separately to remote server 320. In some embodiments, local server 302 is configured to mix audio received from local devices 310, 312 into a single stream that is transmitted as a single audio stream to remote server 320. Telesurgery and telemetry data are discussed further below.

By connecting local devices 310, 312 to a local server 302 instead of to a remote server 320, the quality of service for the telehealth session may be improved. For example, the latency is reduced as the local devices 310, 312 are no longer required to transmit data over an Internet connection. Additionally, the privacy of the data can be preserved, as the data can be manipulated before it leaves the local network 318. The use of a local server 302 also allows for media captured by devices 310, 312 to be recorded at their native resolution, which, in some embodiments, is saved to NAS 306. Furthermore, the use of local server 302 can reduce latency when streaming data from local devices 310, 312, as these devices no longer need to stream data to a remote server over an Internet connection. Accordingly, the quality of service for the telehealth session may be improved as the stability of distribution is less reliant on network connectivity of local devices 310, 312.

In some embodiments, local message broker 308a is configured to manage communication between the various devices within local network 318. As discussed above, the telehealth session may be carried out as a WebRTC session utilizing a publication/subscription architecture. In some embodiments, local message broker 308a utilizes MQTT to manage subscriptions for local devices 310, 312 to the telehealth session. Other message brokers may be utilized without departing from the scope hereof. In some embodiments, local message broker 308a can transmit instructions to local server 302. For example, local message broker 308a may instruct local server 302 to not transmit data received from local media devices 312 until the encoder 304 has applied the necessary obstructions/obscurations (e.g., Gaussian blur). While local message broker 308a is illustrated as associated with local server 302, the functionality of local message broker 308a may be carried out by any device operating in local network 318 in some embodiments. For example, local message broker 308a may instead run on a local client device 310, such as the session hosting client device. In some embodiments, local message broker 308a also handles remote control of local devices 312. As discussed above, participants may use a device control tool to adjust positioning and/or operations of a device within local network 318. Messages sent between client devices 310, 322 for controlling local devices (e.g., cameras 314, displays, etc.) may be managed by local message broker 308a. In some embodiments, a remote message broker 308b operates on or in association with one or more remote servers 320, and the remote message broker 308b may relay messages received from remote client devices 322 to local message broker 308a. In some embodiments, each remote server 320 is associated with a remote message broker 308b. For example, instructions received from a remote client device 322 to adjust the positioning of a camera in the operating remote may be relayed from the remote message broker 308b to the local message broker 308a.

The local client device 310 may be any form of computing device discussed above with respect to FIG. 1. In some embodiments, a local client device 310 operates as the session host for the telehealth session. Local client device 310 may be client device 260 described above. A local participant operating the session-hosting client device 310 may configure various parameters for the telehealth session. For example, the local participant may invite one or more remote participants to participate in the telehealth session. In some embodiments, the local client device 310 is associated with one or more local media devices 312 transmitting media to the local server 302. For example, the one or more local client devices 310 may comprise a web camera and a microphone to stream data of the user operating one or more local client devices 310, as part of the telehealth session.

As mentioned above, local media device 312 may comprise cameras 314, microphones 316, or any other device configured to capture media of the telehealth operation. In some embodiments, local media device 312 may be local media device 268 described above. In some embodiments, the camera 314 may be an IP camera that wirelessly transmits video data to local server 302. As another example, the camera 314 may be on a surgical instrument that is inserted into the patient to capture internal imagery of the patient during surgery. Generally, the camera 314 may be any form of camera and may transmit data to local server 302 wired or wirelessly. Microphones 316 may be disposed around the operating room to capture audio data during the operation. For example, each local surgeon may wear a microphone 316 to capture their audio such that the local surgeon can communicate with the remote participants during the surgery. Various other devices or sensors configured to transmit data to local server 302 are within the scope hereof. For example, sensor data from a monitoring device that is monitoring the patient's vitals may be transmitted as part of the telehealth session and rendered for display on user interface 200. As another example, medical imagery devices may transmit image data to local server 302 for display in a video window 202. For example, an imaging device may obtain imagery of the patient's heart shown and transmit the data as part of the telehealth session as shown in FIG. 2A above.

In some embodiments, the local media device 312 may be a telemetry or telesurgery device as previously discussed. For example, the telemetry device may be a monitoring device for tracking the vitals (e.g., heartbeat) of a patient. In some embodiments, local server 302 is configured to transmit the telemetry data to remote server 320. For example, if local media devices 312 are medical devices that capture telemetry data, the local server 302 may transmit telemetry to remote server 320 for remote users to interpret the telemetry data from the local media device 312. Streaming telemetry data allows remote users to respond immediately to events within the operating room without relying on a user to relay feedback to remote users. In some embodiments, the local server 302 may be configured to send a notification within the telehealth session of events based on telemetry data. In some embodiments, the local server 302 and the remote server 320 are configured to relay instructions from remote client devices 322 or local client devices 310 to the local media device 312. In some embodiments, the local server 302 and the remote server 320 are configured to transmit feedback, such as haptic feedback, from the telesurgery device to remote client devices 322 or local client devices 310. For example, the telesurgery device might be a robotic scalpel. A user of a local client device or a remote client device may control the operation of the robotic scalpel. Haptic feedback transmitted from the robotic scalpel may indicate the physical response of the robotic scalpel.

Media data captured by local devices 310, 312 may be transmitted to local server 302 for distribution to remote server 320. Prior to distributing media to remote server 320, local server 302 may adjust at least a portion of the received media data. In some embodiments, local server 302 adjusts the video stream using encoder 304. For example, the video stream may be adjusted to blur the face (or other body region) of the patient being operated on. Other identifying features, such as tattoos or piercings, may also be adjusted to protect the privacy of the patient. Generally, any portion of the video may be obscured by local server 302. For example, if camera 314 captures video that includes a clock in the operating room, the clock may be obscured to remove time and/or date information relating to the operation. In some embodiments, a Gaussian blur or other blur type is applied. One of skill in the art will appreciate the various adjustments that may be made to the video stream to protect the privacy of the patient. Audio data may also be obscured as discussed above. In some embodiments, encoder 304 is FFmpeg or any other encoder.

In some embodiments, the local server 302 may determine and/or log a computational latency for obscuring the video or performing any other intervention in local media before transmitting the local media out of local network 318. The computational latency may be tracked by logging the processing time it takes for computing the adjustments to the telehealth session to include the intervention. In some embodiments, if at least one of the computational latency or the latency between the local server 302 to a remote server 320 is above a threshold latency, the local server 302 may switch from a more computationally expensive obscuration to a less computationally expensive obscuration to reduce latency. In some embodiments, the detection of excess computational latency causes a change from a first obscuration type to a second obscuration type. For example, instead of using a Gaussian blur, a less computationally expensive graphic overlay, such as a black box, may be rendered over the video portions that are to be obscured.

After adjusting the media received from one or more local media devices 312, local server 302 may transmit the adjusted or obscured media to the remote server 320. In some embodiments, the remote server 320 is configured as a separate instance of the local server 302. For example, the remote server 320 may be a separate JANUS® instance. In some embodiments, remote servers 320 are containerized instances that are dynamically provisioned upon initialization of a telehealth session. In some embodiments, provisioning of remote servers 320 is determined using latency-based testing. Remote servers 320 with the lowest latency between the server and local server 302 may be selected. In some embodiments, the latency-based testing also takes into consideration latency between the remote server 320 and one or more remote client devices 322. In some embodiments, the local server 302 is configured as a minimal version of the remote server 320. For example, local server 302 may have reduced functionality as compared to remote server 320. Remote servers 320 may broadcast the received obscured media to the remote client devices 322.

In some embodiments, local server 302 is configured to transmit the video and/or audio as a simulcast to remote server 320. That is, local server 302 may send media at various qualities as a simulcast to remote server 320, and remote server 320 may in turn forward the media at the quality level required by each remote client device 322. For example, local server 302 may transmit a first copy of a video stream at 4 k, 60 fps, a second copy of the video stream at 1080p, 30 pfs, and a third copy of the video stream at 720p, 30 fps to remote server 320. Remote server 320 may then transmit one of the three copies of the video stream to each remote client device 322 based on the network connectivity of each remote client device 322. In some embodiments, simulcasting of the video streams may be based on the layout of user interface 200. For example, if a video window 202 is enlarged and other video windows 202 are reduced in size, the video stream for the enlarged video window 202 may be broadcast at a higher quality, and the video streams for the reduced video windows 202 may be broadcast at a lower quality. Audio data may also be transmitted using simulcasting techniques. In some embodiments, remote client devices 322 can participate in the session by transmitting audio, video, chat, and telestration data. Accordingly, in some embodiments, remote server 320 may transmit media received from remote client devices 322 to local server 302 as a simulcast to local server 302, and local server 302 simulcasts the media to local client device 310. In some embodiments, the simulcast is a WebRTC simulcast. In some embodiments, the WebRTC simulcast comprises a server 302, 320 encoding three streams at three separate bitrates and transmitting the video stream at one of the three bitrates to a client device 310, 322 based on the network connectivity or bandwidth of the client device 310, 322. In some embodiments, local server 302 and/or remote server 320 operates as a selective forwarding unit to relay streams to client devices 310, 322 based on the needs of the client devices. In some embodiments, local server 302 adaptively streams the telehealth session to remote server 320, as discussed further below with respect to FIG. 3B.

In some embodiments, system 300 comprises a single remote server 320 connected to each remote client device 322 participating in the telehealth session. In some embodiments, system 300 comprises a plurality of remote servers 320, with each of the plurality of remote servers 320 connected to one or more remote client devices 322. When multiple remote servers 320 are employed, local server 302 may replicate and transmit data for the telehealth session to each remote server 320. The use of multiple remote servers 320 may improve resiliency of the telehealth session as one or more of the remote servers may be employed as a warm standby/failover server in the event of a failure of another remote server. Thus, the single point of failure presented by only using a single remote server 320 may be eliminated. Furthermore, the remote servers may be located in distinct geographical locations and connected to remote participants based on a geographic proximity, thereby reducing latency for the remote participants. Other uses and advantages of providing a plurality of remote servers 320 for a telehealth session are discussed further hereinafter.

Multiple remote servers 320 may be utilized for scaling in some embodiments. For example, in some embodiments, a single remote server 320 may be configured to support up to 50 remote client devices 322. Accordingly, when the number of remote client devices 322 nears, reaches, or exceeds 50, an additional remote server 320 may be provisioned and newly-joining remote client devices 322 may be connected to the additional remote server 320. Other threshold numbers (e.g., 10, 20, 100, etc.) for determining when to provision a new remote server 320 are within the scope hereof.

Multiple remote servers 320 may also be utilized when remote participants are located in geographically distinct areas. For example, if a first subset of remote client devices 322 are located in Europe, and a second subset of remote client devices 322 are located in North America, a first remote server 320 located in Europe may be provisioned for the first subset of remote client devices 322, and a second remote server 320 located in North America may be provisioned for the second subset of remote client devices 322. Thus, the latency for the remote client devices 322 may be improved by connecting remote client devices 322 to geographically proximate remote servers 320.

In some embodiments, a remote server 320 may be kept on standby during a telehealth session. For example, all remote client devices 322 may connect to a first remote server 320 for the telehealth session, and a second remote server 320 can be kept on standby and not connected to any remote client device 322. Accordingly, if the first remote server 320 suffers a loss of service or can no longer maintain a requisite quality of service, the remote client devices 322 can be automatically joined to the standby remote server 320 with only a minimum interruption for remote client devices 322. Further, if a standby remote server 320 is provisioned to take over for a failed remote server 320, in some embodiments, a new standby remote server 320 is then provisioned. In some embodiments, local server 302 is configured to forward data to both the in-use remote server 320 and the standby remote server 320 to minimize the disruption in service if the in-use remote server 320 fails. Both the in-use remote server 320 and the standby remote server 320 may record the telehealth session such that, if the in-use remote server 320 fails, the recording is not lost when switching to the standby remote server 320. In some embodiments, each remote server 320 connected to remote client devices 322 has a server on standby. In some embodiments, a single standby remote server 320 is provisioned regardless of the number of in-use remote servers 320. In some embodiments, a standby server is provisioned for a predefined number of remote servers 320. For example, a standby server may be provisioned for every three remote servers 320. In some embodiments, a standby server is provisioned for remote servers based on geographic proximity. For example, if remote servers are located in distinct geographic regions, at least one standby server may be provisioned for each geographic region.

In some embodiments, a backup remote server 320 may be provisioned and ran via a 5G connection in the event of a failure of a remote server 320. For example, if both the in-use remote server 320 and the standby remote server 320 were to fail, system 300 may be configured to provision a remote server 320 ran on a 5G connection. In some such embodiments, once connectivity to one of the in-use or the standby remote server 320 is restored, the remote client devices 322 may be reconnected thereto. It is further contemplated that a 5G server may be provisioned (or held on standby) in the case of failure of local server 302.

In some embodiments, one or more remote servers 320 may be regional or edge servers that are located geographically proximate to the local network 318. In some embodiments, regional remote servers 320 can relay data from local server 302 further out to other remote servers 320. Such an embodiment may be useful when the hospital is located in an area with strong regional Internet connectivity but slower international Internet connectivity. For example, international Internet connectivity may be done via satellite, which may be a limiting factor when conducting a live video conferencing session when remote participants are located in a different country than local network 318 due to latency and/or bandwidth limitation between local server 302 and remote server 320. Accordingly, a regional remote server 320 can be located out of local network 318 but proximal thereto (e.g., within the city or country of local network 318) and relay feeds from local server 302 to other remote servers 320 that are located internationally, or to a satellite that relays the feed to a remote server 320. In some embodiments, an edge server can function as the local server 302. Thus, in some embodiments, it is contemplated that the local server 302 is not physically located in the hospital. Connecting to such edge servers may be done using a VPN to ensure the security of the telehealth session.

As another example, edge remote servers 320 may be used to host a telehealth session when all remote participants are within the same region, such as when remote participants are video conferencing in from hospitals in nearby towns, counties, cities, etc. to the hospital running on local network 318. Accordingly, the need for a remote server 320 that is provisioned from an arbitrary location may be eliminated. If a remote participant located outside of the regional area serviced by the edge remote server 320 joins the telehealth session, an additional remote server 320 can be provisioned for the participant. The use of regional remote servers 320 that are local to the local network 318 may ensure quality of service is maintained for the telehealth session.

In some embodiments, when multiple remote servers 320 are used, each remote server 320 is configured to mix the audio received from the connected remote client devices 322 and forwards the audio mix to local server 302. Local server 302 may then mix the audio into a final audio mix that is distributed to each of the remote servers 320. For example, if two remote servers 320 are used and each remote server 320 receives two audio streams from two remote client devices 322, each remote server 320 may mix the two audio streams and relay the mixed audio stream to local server 302 such that the local server 302 receives a single audio stream from each remote server 320. Once received, local server 302 may further mix the two mixed audio streams into a single audio stream (which may also include any audio received from local media devices 312) and send the single audio stream back to each remote server 320 for broadcasting to the remote client devices 322. To avoid echo, each server 302, 320 may transmit audio with an identifier or other metadata that identifies the source of the audio. Accordingly, if a server 302, 320 receives audio that has already been forwarded from another server 302, 320, the receiving server 302, 320 may refrain from re-forwarding the already forwarded audio to prevent audio echo.

In some embodiments, local server 302 and one or more remote servers 320 are connected to a recording server 324. As discussed further below with respect to FIGS. 5A and 5B, local server 302 and/or remote server 320 may generate recordings of the telehealth session. In some embodiments, servers 302, 320 transmit the recordings to recording server 324 for processing. For example, recording server 324 may synchronize and/or combine the recordings, as discussed below. In some embodiments, local server 302 and/or remote server 320 are configured with the functionality of recording server 324. In some embodiments, recording server 324 resides within local network 318.

Figure 3B:
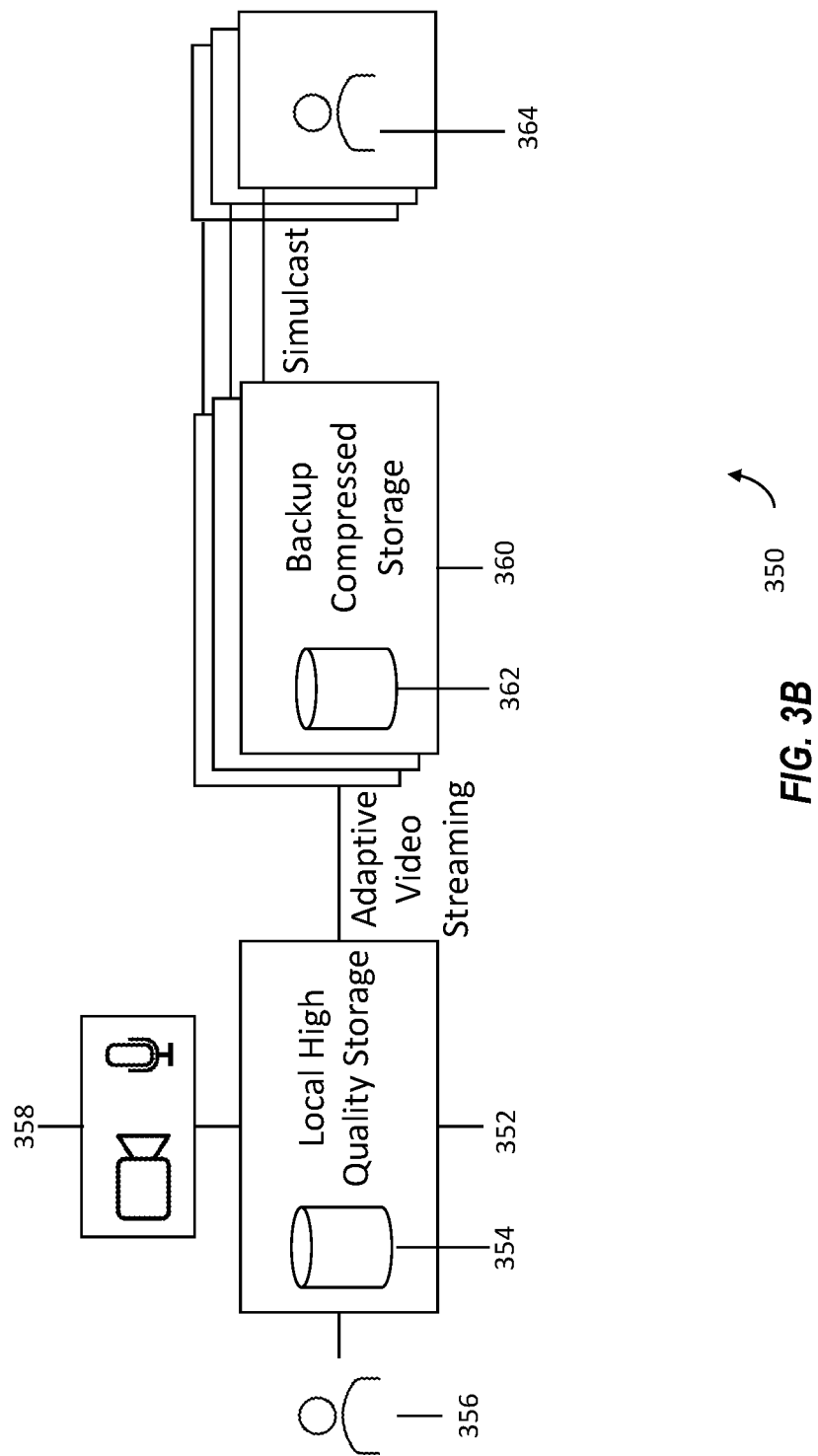
FIG. 3B depicts the hybrid media distribution system for some embodiments.

FIG. 3B illustrates a system 350 for carrying out embodiments of the present disclosure. System 350 may be substantially similar to system 300 described above. System 350 illustrates how broadcasting of the telehealth session may be performed in order to provide a more resilient and secure system. System 350 may comprise a local server 352, local storage 354, one or more local participants 356, and one or more local client devices 358. Local server 352 may correspond to local server 302 discussed above. Local storage 354 may correspond to NAS 306 discussed above. The one or more local client devices 358 may correspond to local client devices 310 discussed above.

Local server 352 may be communicatively coupled to one or more remote servers 360, which may correspond to remote servers 320. At least one of the remote servers 360 may comprise a remote storage 362 for storing data associated with the telehealth session. In some embodiments, each remote server 360 includes remote storage 362. Each of the one or more remote servers 360 may broadcast data to one or more remote participants 364, corresponding to remote client devices 322 discussed above. While not shown in FIG. 3B, it will be appreciated that other components illustrated with respect to FIG. 3A may also be present in FIG. 3B, such as message brokers 308a, 308b, or any other component discussed above with respect to system 300.

As shown, local server 352 may transmit data for the telehealth conference to the one or more remote servers 360. Local server 352 may replicate the data transmission for each remote server 360 that has been provisioned for the telehealth session (including any standby servers, if present). In some embodiments, local server 352 employs adaptive streaming techniques when transmitting the telehealth session. The adaptive streaming may comprise local server 352 adjusting one or more video quality parameters for the telehealth session based on network conditions. For example, one or more of the frame rate, bit rate, or resolution of the telehealth session may be adjusted by local server 352 responsive to changes in network quality. For example, a rural hospital may have a poor network connection from local server 352 to a remote server 360. Accordingly, local server 352 may transmit the telehealth session to the remote server 360 at a lower frame rate to compensate for the poor network connection.

When connected to greater than one remote server 360, local server 352 may adaptively stream the telehealth session to each remote server 360 such that different remote servers 360 may receive the telehealth session streamed at different quality levels. For example, local server 352 may be connected to a first remote server 360 and to a second remote server 360, and the connection between local server 352 and the second remote server 360 may be worse than the connection between local server 352 and the first remote server 360. Accordingly, local server 352 may transmit the telehealth session to the first remote server 360 at a first quality level and, when it is detected that the connection between local server 352 and the second remote server degrades, local server 352 may adjust the streaming to second remote server 360 while maintaining the quality transmitted to first remote server 360.

In some embodiments, local server 352 is configured to preferentially adjust one quality parameter over the other quality parameters (e.g., frame rate, bit rate, resolution). That is, responsive to determining that an adjustment to a video quality parameter is needed, local server 352 may adjust one of the bit rate, the frame rate, or the resolution before adjusting the other parameters. For example, local server 352 may preferentially adjust the frame rate before making changes to either the bit rate or the resolution. Degrading the frame rate before the bit rate or the resolution allows for the image quality of the telehealth session to be maintained, which may be important for remote participants who are viewing the telehealth session and may be assisting the local surgeons in performing the procedure. In some embodiments, either the bit rate or the resolution may be adjusted preferentially over the frame rate. In some embodiments, the telehealth session is configured to be streamed at 30 fps, and local server 352 decreases the frame rate to 15 fps before adjusting either the bit rate or the resolution. In some embodiments, the telehealth session is configured to be streamed at 24 fps, and local server 352 decreases the frame rate to 12 fps before adjusting either the bit rate or the resolution.

In some embodiments, once the frame rate is decreased to a threshold frame rate, if further adjustments need to be made by local server 352 to the adaptive streaming of the telehealth session, at least one of the bit rate or the resolution are then adjusted. The threshold frame rate may be 12 fps, 15 fps, or any other frame rate and may be predefined by a user, such as the session host. By maintaining a minimum threshold frame rate, the latency of the telehealth session may be prevented from excessively increasing. For example, when streaming at 30 fps, 30 ms of latency is inherent in the telehealth session and lowering the frame rate to 15 fps doubles the latency to 60 ms. Accordingly, if a further frame rate reduction occurs, the latency would likewise increase. As such, defining a minimum frame rate threshold allows for latency due to the frame rate to be controlled. Similarly, if either the bit rate or the resolution is adjusted before the other parameters, a minimum bit rate or resolution may be set that will prevent further degradations of the parameter and result in a different parameter being adjusted.

Each remote server 360 may be communicatively coupled to a respective plurality of remote participants 364, and each remote server 360 may broadcast the received data stream(s) for the telehealth session to the respective plurality of remote participants 364. As previously discussed, each remote server 360 may support 50 remote participants 364, although embodiments of the present disclosure may include fewer or greater remote participants 364 connected to a remote server 360 without departing from the scope hereof. In some embodiments, one or more of the remote servers 360 is configured to simulcast the telehealth session based on the network quality of each remote participant 364. The simulcast may be a WebRTC simulcast wherein three bitrates of the telehealth are generated, and one of the three bitrates is streamed to a remote participant based on the needs of the remote participant 364 as previously discussed. System 350 may employ other adaptive bitrate streaming techniques (e.g., MPEG-DASH, etc.) without departing from the scope hereof.

Remote participants 364 may participate in the telehealth session as previously discussed. Remote participants 364 may send any combination of audio, video, or chat/telestration data. The remote participants 364 may transmit the data to their respective remote server 360, and the remote server 360 routes the data to the local server 352. Aspects of the present disclosure may reduce latency in the telehealth session by providing a single local server 352 connected to the participants 356 (i.e., client devices) and local media devices 358. Because there may be multiple one or more local participants 356 viewing the telehealth session within the hospital network, latency may be reduced as each of the one or more local participants 356 only connect to local server 352 rather than each participant 356 separately connecting remote server 360. Accordingly, the download bandwidth requirements are reduced, and a single connection to remote server 360 made by local server 352 can be used to receive telehealth session data from remote servers 360, which may then be broadcast the data to the participants 356.

As discussed in further detail below, embodiments of the present disclosure may provide for improved reliability in generating recordings of the telehealth session. Recordings of the telehealth session may be used for record keeping purposes, teaching/lecturing purposes, and the like. Maintaining a high-quality recording of the session provides for improvements in teaching, lecturing, training, etc. of medical procedures.

As shown, each local server 352 and the one or more remote servers 360 includes storage 354, 362. Storage 354, 362 may be configured to store recordings of the telehealth session, among other data relating thereto, as will be appreciated by one of skill in the art. In some embodiments, local storage 354 is configured to store a high-quality version of at least a portion of the telehealth session. The high-quality version may include recordings from some or all of the local media generated within local network 318 at a native quality. For example, if one or more local client devices 358 includes a 4 k camera capturing the surgical operations at 30 fps, local storage 354 may include a native recording of this data. Meanwhile, when data captured from the 4 k camera is streamed to remote server 360, the data will likely be streamed at a lesser quality (e.g., at 720p and 15 fps) because of network constraints. Thus, by routing data captured by one or more local client devices 358 to local server 352, a high-quality recording of the telehealth session may be persevered regardless of the quality of the connection between local server 352 and remote server 360. Local storage 354 may also record incoming data transmitted from remote server 360, such as any data from one or more remote participants 364.

Remote storage 362 may also record data for the telehealth session. The recording generated at remote storage 362 may serve as a backup for the recording generated at 354 in some embodiments. The remote recording may be a compressed recording as the data from one or more local participants 356 and one or more local client devices 358 may be compressed when transmitted from local server 352 to remote server 360. Recordings stored at remote storage 362 may be transmitted to local storage 354 or another location (e.g., recording server 324) for combining the recordings to generate a synchronized recording, as discussed further below. In some embodiments, at least one remote participant 364 is configured to generate a local recording of any data generated by the at least one remote participant 364. The local recording may be later uploaded to remote server 360 for generating the combined recording.

FIG. 4 illustrates an exemplary method 400 for carrying out a telehealth session using a hybrid media distribution system 300 in accordance with embodiments of the present disclosure. At step 402, media data from one or more local media devices 312 may be received at the local server 302. The media data may comprise audio data and/or video data of the operation being performed. In some embodiments, media data is also received from local client devices 310. For example, a local client device 310 may have an associated web camera and microphone to stream audio and video of a user operating the local client device 310. The media data may also include chat and/or annotation data inputted via local client device 310. As discussed previously, sending media from devices 310, 312 to a local server 302 instead of to a remote server 320 can lower latency for the telehealth session. Eliminating the requirement for local devices 310, 312 to connect to a remote server 320 may be beneficial for areas where Internet connectivity is poor.

Next, at step 404, local server 302 may obscure a portion of the received, local media data. The data may be obscured in various ways. For example, the obscuring may comprise blurring, by encoder 304, identifying features of the patient. In some embodiments, local message broker 308a instructs local server 302 to prevent relaying the media data until encoder 304 has modified the data. In some embodiments, a participant of the telehealth session defines one or more obscure regions 210 for a video stream. In some embodiments, only the session host can define obscure region 210. By obscuring data within local network 318, privacy of the patient may be preserved before the media data leaves the local network 318. In some embodiments, one or more firewalls (not shown) associated with local network 318 may prevent devices located outside of the hospital from connecting to local server 302.

At step 406, local server 302 may transmit the obscured media to one or more remote servers 320. As previously discussed, each remote server 320 may be a separate instance of the local server 302. When multiple remote servers 320 are employed, local server 302 may transmit data for the telehealth session to each remote server 320 separately. In some embodiments, local server 302 forwards the data to an edge server, and the edge server propagates the data to other remote servers 320. In some embodiments, media for the telehealth session is sent on at least three separate channels: a channel for audio data, a channel for telestration/chat data, and one or more channels for each video stream (i.e., one channel per video stream). It is contemplated that telestration data and chat data may have separate channels. In some embodiments, local server 302 adaptively streams the telehealth session to the remote servers 320 as previously discussed. When an adjustment to the telehealth session quality needs to be made, local server 302 may lower the frame rate before either the bit rate or the resolution.

At step 408, the remote server 320 may broadcast the obscured media to one or more remote client devices. In some embodiments, remote server 320 broadcasts the obscured media as a simulcast, which may be a WebRTC simulcast wherein three encodings are generated, and an encoding of the three encodings are sent to each remote client device 322 based on the quality of the connection between the remote client device 322 and remote server 320. Because the media data may be at least partially obscured, the remote participants may be unable to identify the patient in the telehealth session, thereby preserving the privacy of the patient. As previously discussed, remote participants may also participate in the telehealth session by streaming audio and/or video, along with transmitting chat and telestration data. Accordingly, at step 410, the remote client devices 322 may transmit media data to the remote servers 320. The session host may configure which (if any) remote participants can stream video and/or audio data as part of the telehealth session.

At step 412, the remote server 320 may transmit the received media data to the local server 302. Data received from a remote client device 322 may also be relayed by the remote server 320 to other remote client devices 322 connected to the remote server 320. In some embodiments, remote server 320 is configured to mix audio streams from each remote client device 322 into a single audio stream that is transmitted to local server 302.

Lastly, at step 414, the local server 302 may broadcast the remote media data to the one or more local client devices 310. As previously discussed, by reducing the number of connections from local network 318 to remote server 320 to a single connection, the bandwidth requirements of local network 318 are reduced, which may improve the resiliency of the telehealth session to the quality of local network 318. In some embodiments, local server 302 also transmits the data received from a first remote server 320 to other remote servers 320. For example, local server 302 may relay data received from remote server 1 to remote server N.

It will be appreciated that the steps of the method 400 may occur in various orders and may occur simultaneously or near simultaneously. For example, one or more local client devices 310 and remote client devices 322 may transmit media data to local server 302 and remote servers 320, respectively, at the same time. Furthermore, while discussed with respect to system 300, one of skill in the art will appreciate that method 400 may also be carried out by system 350 without departing from the scope hereof.

Recording of the Telehealth Session

Embodiments described herein may also provide for improved recordings of telehealth sessions that are resilient to changes in network performance and/or may be synchronized such that the recording reflects the telehealth session at the point of data capture for each recorded data stream, irrespective of network latencies for transmitting data between servers 302, 320. Recording telehealth sessions can be useful for instructional use, for example. In some embodiments, multiple recordings of the telehealth session are created. In some embodiments, each video stream is recorded, and a composite recording is created from the individual recordings of the video streams. For example, if the telehealth session comprises four video streams, a recording may be created for each of the four video streams, and a fifth recording may be generated that is a composite of the four video streams. In some embodiments, the composite video is generated as a reproduction of user interface 200 during the telehealth session. For example, if during the telehealth session, a video window 202 is maximized and other video windows 202 are scaled accordingly, the recording may include the adjustment to the user interface 200.

In some embodiments, a separate recording of each video stream is made that comprises annotations 206. Thus, if each of the four video streams is annotated on at any point during the telehealth session, four separate recordings of the video streams with the annotations 206 overlaid are made. In some embodiments, a composite annotated recording is generated comprising a composite of the separate annotation recordings. Thus, in the example case where the telehealth session comprises four video streams, ten recordings may be generated: four recordings corresponding to each video stream without annotations, a composite recording of the four recordings without annotations, four recordings corresponding to the annotations made on each of the four video streams, and a composite recording of the four recordings of the annotations. In some embodiments, the session host or another user can define which recordings should be generated. For example, the session host may elect to only generate the non-annotated composite video recording.

In some embodiments, local server 302 generates one or more of the above-described recordings of the telehealth session for later playback. For example, the local server 302 may generate the recording of each video stream (including a corresponding audio stream, in some embodiments), which may be used to generate the composite recording. By generating a recording by local server 302, it may be guaranteed that media captured by local devices 310, 312 is saved at the native quality. Thus, a highest quality recording of the medical procedure as captured on site may be preserved. Furthermore, recording at local server 302 ensures that data captured in the operating room is not lost in the event of a loss of Internet connection. For example, without the use of a local server 302, if devices in the operating room lost connection to a remote server hosting the telehealth session, all media captured during the period of lost connection would be lost from the recording. In some embodiments, the recording made at local server 302 is saved to NAS 306 or in any other memory location.

In some embodiments, both local server 302 and at least one remote server 320 are configured to record the telehealth session as discussed above with respect to FIG. 3B. When multiple remote servers 320 are used, a single remote server 320 may be configured to make the remote recording. In some such embodiments, the remote server is the server with the highest number of connected remote client devices 322. In other embodiments, each remote server 320 records at least a portion of the session. For example, each remote server 320 may record a video stream received from a connected remote client device 322. Recordings made by local server 302 are referred to hereinafter as local recordings, and the recordings made by remote servers 320 are referred hereinafter to as remote recordings. In some embodiments, local server 302 and remote server 320 transmit recordings to a recording server 324 for further processing, such as compositing of the individual video streams. In some embodiments, local server 302 and/or remote server 320 carry out the functions of recording server 324. In some embodiments, a combined recording is generated by combining various portions of the recordings made at each of local server 302 and the at least one remote server 320. For example, when transmitting telehealth session data from local server 302 to a first remote server 320 and a second remote server 320, a packet comprising a frame may be lost in transmission to the second remote server 320 while arriving at the first remote server 320. As such, when combining recordings from the first remote server 320 and the second remote server 320, the frame lost at the second remote server 320 may be replaced with the corresponding frame at the first remote server 320.

In some embodiments, the local recording comprises only native feeds from each device operating on the local network 318. Thus, the local recording may exclude the data feeds received from remote client devices 322. In some such embodiments, the remote server 320 records all feeds, including the data recorded by the local client devices in local network 318. Due to the remote servers 320 receiving data from local server 302 over an Internet connection, it is likely that the data from the devices in the local network 318 will be transmitted at a lower quality than the data was captured. For example, if the camera 314 is a 4 k camera, the video feed will likely be downgraded (e.g., to 1080p) when local server 302 transmits the video stream to remote server 320. Such a scenario is especially likely when the hospital is in an area of relatively poor Internet quality. However, because the data from local devices 310, 312 in local network 318 are also recorded locally by local server 302, the native quality of the data can be maintained without degradation. Accordingly, when the local recording and the remote recording are combined to generate the composite recording, the video stream corresponding to media captured by local media devices 312 may be taken from the local recording, and the video stream corresponding to media captured by remote client devices 322 may be taken from the remote recording.

In some embodiments, recording server 324 is configured to generate the composite recording from the local recording(s) and the remote recording(s). The composite recording, in some embodiments, may comprise the highest quality portion of the recording generated from the local recording and the highest quality portion from the remote recording made by one or more remote servers 320. For example, the composite recording may be a composite of the video streams from in-OR devices as captured by local server 302 (and optionally saved to NAS 306) and the video streams transmitted by remote client devices 322 as captured by remote server 320. When combining the local recording and the remote recording, recording server 324 may synchronize the two recordings. Due to the latency between local server 302 and remote server 320, the local recording and the remote recording may not be synchronized when transmitted to recording server 324. For example, camera 314 may stream video to local server 302 at 60 fps, which may be natively stored to NAS 306 and later sent to recording server 324. However, due to a poor network connection, for example, a remote client device 322 may stream the video to remote server 320 at 30 fps. Accordingly, the recordings may need to be adjusted to account for the differences in frame rate due to latency. In some embodiments, frames from the recording with a higher frame rate are dropped to match a frame rate of a lower frame rate recording. In some embodiments, frames from the lower frame rate recording are repeated to match the higher frame rate recording.

Figure 5A:
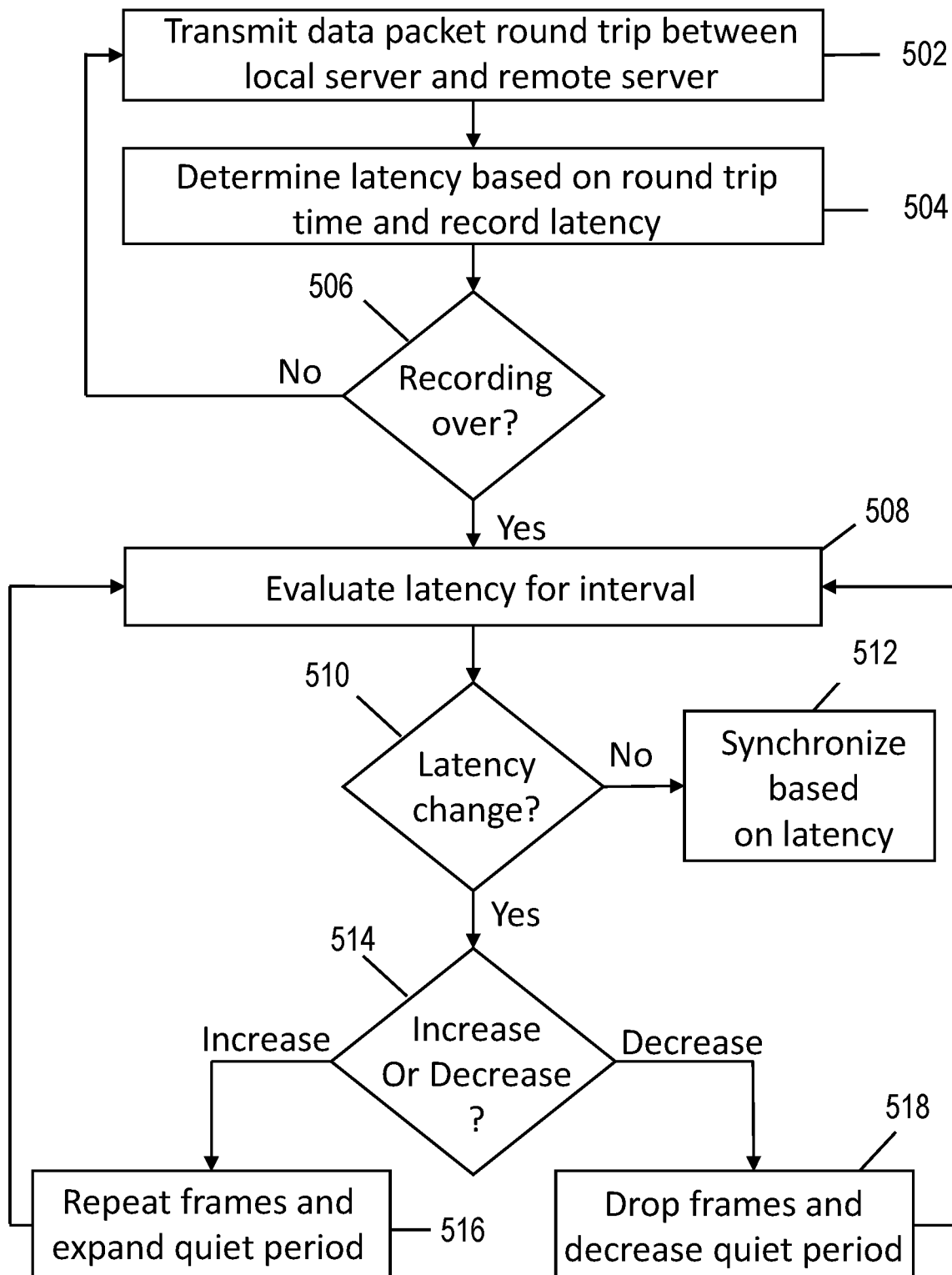
FIG. 5A depicts a first method for synchronizing a local recording and a remote recording of the telehealth session for some embodiments.

FIG. 5A illustrates an exemplary method 500 for synchronizing the local recording and the remote recording such that the local recording and the remote recording can be combined to generate the composite recording for some embodiments of the present disclosure. Method 500 may begin at step 502, where a data packet or ping may be transmitted round trip from local server 302 to remote server 320 and back to local server 302 to determine the latency between the servers 302, 320. In some embodiments, the data packet is sent periodically throughout the telehealth session. For example, the data packet may be sent about every 200 ms, or at any other interval. When multiple remote servers 320 are used to manage the telehealth session, a data packet may be sent to each remote server 320. Likewise, if a remote server 320 is kept on standby in the event of a failure of an in-use remote server 320, a data packet may also be transmitted to the standby remote server 320. When determining latency between local server 302 and more than one remote server 320, data packets may be sent to each remote server 320 simultaneously, or data packets may be sent at different intervals for each remote server 320.

Next, at step 504, the latency between local server 302 and remote server 320 may be determined based on the round trip time for the data packet. In some embodiments, the latency is determined by assuming that the latency is equivalent for transmitting data from local server 302 to remote server 320 as for transmitting from remote server 320 to local server 302. Thus, the round trip time may be halved to determine the latency. In some embodiments, a first latency is determined for the time to transmit a ping from local server 302 to remote server 320, and a second latency is determined for the time to return the ping from remote server 320 to local server 302. Accordingly, in some embodiments, the time at which the data packet was transmitted by local server 302, the time at which the data packet was acknowledged at remote server 320, and the time at which the returned data packet is acknowledged back at local server 302 are evaluated to determine first and second latencies. The latency may be logged or otherwise stored to synchronize the recordings after the telehealth session ends. In some embodiments, remote server 320 initiates the sending of the data packet and logs latency between local server 302 and remote server 320.

Processing may then proceed to test 506 where it may be determined whether recording is over. Recording may be over when the telehealth session ends or upon receiving an instruction to end recording, such as via user interface 200. If the recording is not over, processing may return to step 502, and another data packet may be transmitted to determine the current latency between local server 302 and remote server 320. As discussed above, the data packet may be transmitted in intervals throughout the telehealth session. For example, the data packet may be transmitted every 200 ms. If recording has ended, processing may proceed to step 508. In some embodiments, the latency between local server 302 and remote server 320 is logged throughout the telehealth session regardless of whether the session is being recorded.

Synchronization of the local recording and the remote recording may begin at step 508 once recording is complete. In some embodiments, synchronization of the recording takes place after the telehealth session is complete. At step 508, an interval of the recording may be evaluated based on the latency. As discussed above, the latency may be logged throughout the telehealth session such that the log may be used after the session for synchronization.

Next, at test 510, it may be determined whether there was a change in latency as compared to one or more previous intervals. As discussed previously, a change in latency may lead to a change in the copy of the video stream that is simulcasted, which may result in recordings made at differing frame rates. If there is not a change in latency, processing may proceed to step 512, and the recordings may be synchronized based on the latency. In some embodiments, the remote recording is synchronized to the local recording by adjusting timestamp for the frames in the remote recording based on the latency. For example, if the latency for an interval of the recording containing 12 frames was determined to be 5 ms, timestamps for the 12 frames may be shifted by 5 ms to match the local recording.

If, at test 510, a change in latency is determined, processing may proceed to test 514. In some embodiments, the latency must change by above a threshold amount (e.g., 10 ms, 50 ms, etc.) to satisfy test 510. In some embodiments, a threshold number of intervals must have a change in latency in the same direction (i.e., increase or decrease) to satisfy test 510. For example, three or more consecutive intervals that have an increase in latency relative to a previous iteration must be present to satisfy test 510. In some embodiments, the change in latency that satisfies test 510 is the change that results in the video to be streamed at a different frame rate. Other variations of determining whether to adjust the synchronization of the recordings based on a change in latency will be readily apparent to one of skill in the art.

At test 514, it may be determined whether the change in latency is an increase or a decrease in latency. If the change is an increase, processing may proceed to step 516. At step 516, frames may be repeated in the remote recording to account for the increase in latency causing a lower frame rate. By repeating frames in the remote recording, the remote recording may be modified to match the frame rate and be synchronized to the local recording. The recorded audio may be synchronized in a similar manner by increasing a period of quiet within the remote recording to synchronize the audio to the local recording. Alternatively, it is contemplated that frames from the local recording may be dropped to match the frame rate of the remote recording, and the quiet periods in the audio may be shortened. If, at test 514, it is determined that the latency change is a latency decrease, processing may proceed to step 518. At step 518, one or more frames may be dropped from the remote recording to account for the decrease in latency. For example, if the remote recording is at a higher frame rate than the local recording, frames from the remote recording may need to be dropped to match the frame rate of the local recording. Likewise, to synchronize the audio, a period of quiet may be reduced when there is a decrease in latency.

Figure 5B:
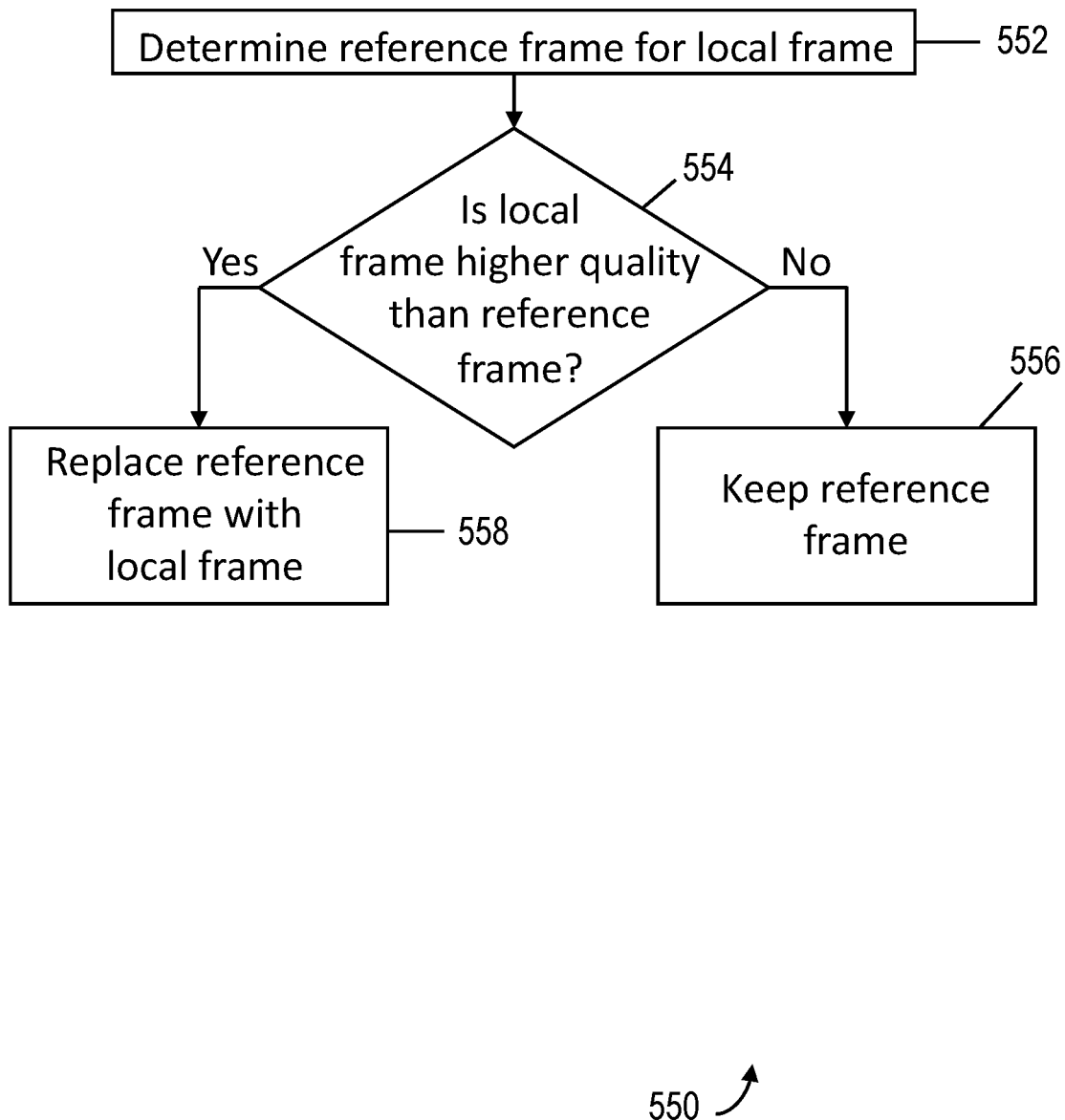
FIG. 5B depicts a second method for synchronizing the local recording and the remote recording of the telehealth session for some embodiments.

FIG. 5B illustrates a method 550 for synchronizing and combining the remote recording and the local recording by using a reference recording for some embodiments of the present disclosure. In some embodiments, the remote recording may be used as a reference recording and compared against the local recording to synchronize and/or combine the recordings. Method 550 may begin at step 552 where, for a frame in the local recording, a corresponding frame in the reference recording is identified. The reference frame may be identified using various techniques. For example, computer vision techniques may be used to compare frames from the reference recording with frames from the local recording to find the closest match for each frame. In some embodiments, frames are matched based on timestamps for the recording. For example, it is contemplated that the local recording and the remote recording can be synchronized as discussed above with respect to method 500. The corresponding reference frame for a local frame may then be determined based on two frames sharing the same or substantially the same timestamp. In some embodiments, each recording server 320 that generates a recording of the telehealth session is analyzed to determine the reference frame. Thus, if a first remote server 320 is missing a reference frame in the recording, the reference frame from a second remote server 320 that is not missing may be utilized.

Next, at test 554, the local frame may be compared to its corresponding reference frame to determine whether the local frame is of a higher quality than the local frame. In some embodiments, reference frames from multiple remote servers 320 are compared, and the highest quality reference frame is compared against the corresponding frame at local server 302. In some embodiments, comparing the local frame to the reference frame comprises comparing at least one of a resolution or a frame rate of the two frames. If, at test 554, it is determined that the local frame is not of a higher quality than the corresponding reference frame, processing may proceed to step 556, and the reference frame is kept in the recording. For example, if neither the resolution or the frame rate of the local recording is higher than that of the corresponding reference frame, the local frame may be determined to be of lower quality than the reference frame, and the reference frame is kept in the recording. This may be the case where the frames are being compared for a recording of a video stream originating from a remote client device 322, for example, as the quality of the video stream may degrade when transmitting from remote server 320 to local server 302 such that remote server 320 has the highest quality recording of the video stream. Processing may then proceed back to step 552 to process the next frame in the recording.

If, at test 554, it is determined that the local recording is of a higher quality of the reference recording, processing may proceed to step 558, and the local frame may replace the reference frame. In some embodiments, if either the resolution or the frame rate is higher in the local frame than the reference frame, it may be determined that the local frame is higher quality than the reference frame. Processing may then proceed back to step 552 to evaluate the next frame. It will be appreciated that method 550 may be performed using the local recording as the reference recording.

When replacing frames as described above with respect to FIG. 5B, any annotations 206 present in the recording may need to be resynchronized. In some embodiments, if the local frame that is replacing a reference frame is a repeated frame (e.g., when inserted into the recording to account for an increase in latency), the annotation may not be added until a non-repeated frame is detected. Once a non-repeated frame is detected, the annotation 206 may be overlaid on or written into the recording. In some embodiments, the aspect ratio of an annotation 206 is adjusted to scale the annotation 206 for the recording. The resolution may also be upsampled or downsampled to match the resolution of the 206 to the resolution of the frame.

In some embodiments, the composite recording is synchronized such that each data feed in the recording is played to match the time of data capture for each feed. That is, the recording for each data feed may be time-shifted in the composite recording based on the latency for each data feed during the recording of the telehealth session. For example, where the latency for video captured in hospital 250 to be displayed on remote client devices 322 is 15 ms, the recording of the video feed the video captured in hospital 250 may be shifted by 15 ms. This, therefore, allows the synchronized recording to comprise a recording in which the events in the hospital 250 and the reaction to said events by a remote user operating remote client device 322 are synchronized and displayed at the same time in the recording. It will be appreciated that generally any type of data that is transmitted recorded during the telehealth session may be synchronized in accordance with the present teachings. As another example, a telehealth session may include the use of generated 3D data. The 3D data may be a rendering of a patient's organ, LIDAR data, point cloud data, or the like, that may be useful in a telesurgery application. A local client device 310 may be configured to generate this 3D data, for example, and the latency between the local client device 310 transmitting the 3D data to local server 302 (or the latency for the data to reach remote client devices 322, for example) may be used to generate the synchronized recording.

Figure 6:
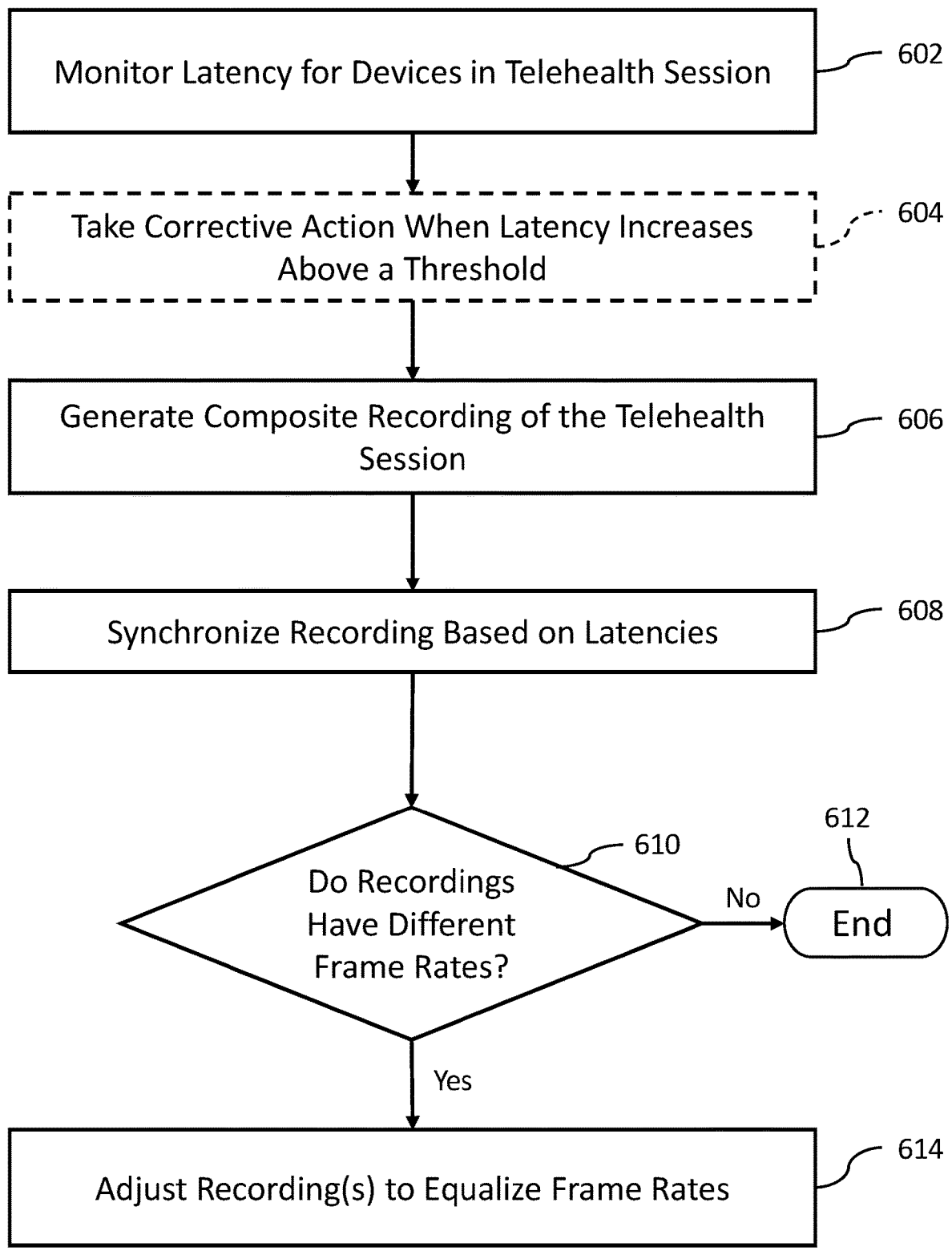
FIG. 6 depicts a method for calculating latency between a local media device and the local server and notifying of changes for some embodiments.

FIG. 6 illustrates an exemplary method 600 for monitoring latencies of devices in telehealth sessions and generating a synchronized recording based on the latencies in accordance with embodiments of the present disclosure. A plurality of latencies may be monitored during the telehealth session, including both a plurality of the same latency for the duration or portion of the telehealth session (e.g., monitoring the latency between local server 302 and remote server 320 during the telehealth session), along with a plurality of latency types (e.g., latency for each of a video feed, an audio feed, and sensor feedback from a surgical device). As previously discussed, a combined recording of the telehealth session may be generated that comprises both local and remote recordings of data generated during the telehealth session. The combined recording may be rendered as a replica of the user interface 200 shown during the telehealth session and/or the combined recording may allow for individual data feeds to be selectively viewed. For example, within a user interface for viewing the combined recording, a video feed may be selected from the composite view to view only the selected video feed. The combined recording may be synchronized such that each recorded data feed is synchronized to the point of data capture to obviate discrepancies in events participant was reacting to due to latency. Syncing the recordings may also enable the video feed to exactly match the time at which telemetry data was captured. For example, if a heartbeat sensor generates log emissions at constant intervals, a video recording of the patient wearing the heartbeat sensor may be synchronized to the emission of the logs, removing any latency from capturing the video and transmitting the video to local server 302.

Method 600 may begin at step 602 where latencies for devices participating in the telehealth session are monitored. In some embodiments, a latency is monitored for each device that transmits data to another device that is also participating in the telehealth session. In some embodiments, the latency is monitored for a single hop (e.g., from telesurgery device 262 to local server 256), for multiple hops (e.g., from telesurgery device 262 to local server 256 and then to a remote server), or a combination thereof. For local devices 310, 312, the latency may be tracked between the devices 310, 312 and local server 302. In some embodiments, local devices 310, 312 transmit a message to each device in local network 318 that is also returned to the sending device 310, 312. Accordingly, when the sending device receives the message back (i.e., from local server 302), the latency between the sending device and local server 302 may be determined based on when the message was transmitted by the sending device and when the message was received back at the sending device. For example, the sending local media device 312 may be a telesurgery device such as a robotic scalpel. The robotic scalpel may have a transceiver or the like to transmit a message to the message broker with haptic sensor data that includes a timestamp, which may be logged such that the latency between the local media device 312 and local message broker 308a may be determined. Remote devices 322 may likewise have their latency monitored by remote server 320 by transmissions of messages (e.g., data packets, echo pings, etc.) that are timestamped, thereby enabling latency to be determined based on the time stamps. Generally, any method of monitoring latency for any device participating in the telehealth session (e.g., local client devices 310, local media devices 312, remote client devices, servers 302, 320, telemetry devices, etc.) is within the scope hereof.

At optional step 604, corrective action may be taken in response to determining that a latency for a device has increased above a threshold. In some embodiments, the corrective action is configured to mitigate unsafe telehealth operations due to high latencies for device(s) in the telehealth session. For example, if a remote user operating remote client device 322 is remotely controlling a telesurgery device and the remote client device 322 experiences increased latency, the remote user may be viewing the surgical operation at a delay and instructions for controlling the telesurgery device may be based on old audio/video data of the telesurgery operation that are no longer reflective of the current state of the telesurgery. Accordingly, the corrective action may be used to prevent the instructions generated by the remote user from being carried out by the surgery device. In some embodiments, the corrective action comprises a notification generated by a server 302, 320 and transmitted to the remote client devices 322. In some embodiments, each device monitors the device's own latency and accordingly may broadcast a message to one or more other devices or servers of the latency increase.

Processing may proceed to step 606 where a combined recording of the telehealth session is generated. The combined recording may comprise the remote recording(s) and the local recording(s) received from each device 310, 312, 322 as previously discussed with respect to FIGS. 5A-5B.

Thereafter, at step 608, the combined recording may be synchronized based on the latencies monitored during the telehealth session. The combined recording may be synchronized such that each data feed is played in the recording at a time corresponding to the actual time of data captured as opposed to when the data was streamed as part of the telehealth session. Thus, for example, the local recordings of media captured in hospital 250 may have a latency of 15 ms between the media being captured, local server 302 applying any obscurations or other processing, local server 302 transmitting the media to remote server 320, and remote server 320 forwarding the data to the remote client devices 322. Accordingly, when generating the synchronized recording, the local recording may be displayed 15 ms earlier in the synchronized recording to reflect when the local media data was actually captured.

Next, at test 610, it may be determined whether the recordings have different frame rates. As previously discussed, the recordings may have different frame rates due to network latency, among other factors. For example, local server 302 may record local media data at a high frame rate (e.g., 30 fps), while remote client devices 322 may transmit data to remote server 320 at a lower frame rate (e.g., 15 fps) due to latency between remote server 320 and remote client devices 322. If, at test 610, it is determined that the recordings do not have different frame rates, method 600 may end 612.

If, at test 610, it is determined that the recordings do have different frame rates, processing may proceed to step 614, where the recordings may be adjusted to equalize the frame rates. In some embodiments, step 614 is substantially similar to step 516 or step 518 discussed above, where frames may be repeated and audio may be adjusted to account for increases in latency. For example, for a remote recording having a frame rate of 15 fps, each frame may be repeated once to double frame rate to 30 fps to match that of a local recording having a frame rate of 30 fps. In some embodiments, frame averaging techniques are employed to adjust the frame rate of a data stream in a recording.

While embodiments herein have been discussed with respect to telehealth sessions, it will be appreciated that the embodiments are not limited to telehealth. For example, it is contemplated that the above-described architecture may be useful in any scenario in which data transmitted in a video conference needs to be secured. As another example, if a video conference is held in a location where a portion of the participants are in a region with strong local Internet connectivity and a poor international connectivity and a portion of participants are located internationally, the use of an edge video server may be useful to reduce the network requirements of the local participants.

Although the present disclosure has been described with reference to the embodiments illustrated in the attached drawing figures, it is noted that equivalents may be employed and substitutions made herein without departing from the scope of the present disclosure as recited in the claims.

The invention claimed is:

1. A hybrid media distribution system for a telehealth session, comprising:
a local server operating on a local network, the local server disposed in a location associated with a patient;
at least one local media device connected to the local network and configured to capture local media of the telehealth session; and
at least one remote server operating on a remote network, the at least one remote server not disposed in the location associated with the patient,
wherein the local server comprises at least one local server processor configured to execute computer-executable instructions to:
receive the local media from the at least one local media device;
broadcast the local media to the at least one remote server; and
generate a first video recording comprising the local media captured by the at least one local media device,
wherein the local media comprises at least one first video stream;
wherein the at least one remote server comprises at least one remote server processor configured to execute further computer-executable instructions to:
receive the local media from the local network;
broadcast the local media to at least one remote participant;
generate a second video recording comprising telehealth session data received from the at least one remote participant,
wherein the telehealth session data comprises at least one second video stream;
log a first plurality of latencies between the local server and the at least one remote server;
log a second plurality of latencies between the at least one remote server and the at least one remote participant; and
generate a synchronized recording of the telehealth session based on the first video recording, the second video recording, the first plurality of latencies, and the second plurality of latencies,
wherein the synchronized recording includes the at least one first video stream from the first video recording and the at least one second video stream from the second video recording, and
wherein the synchronized recording is synchronized to a time of data capture of the at least one first video stream by shifting in time the at least one second video stream based on at least one of the second plurality of latencies.

2. The hybrid media distribution system of claim 1, wherein logging the first plurality of latencies comprises determining each latency of the first plurality of latencies based on a data packet sent between the local server and the at least one remote server.

3. The hybrid media distribution system of claim 1, wherein the at least one local server processor is further configured to:
apply at least one obscuration to the at least one first video stream prior to transmitting the local media to the at least one remote server.

4. The hybrid media distribution system of claim 3, wherein each of the first plurality of latencies is a combined latency comprising a network latency between the local server and the at least one remote server and a computational latency associated with applying the at least one obscuration to the local media.

5. The hybrid media distribution system of claim 1, wherein the first plurality of latencies comprises a plurality of video latencies associated with the at least one first video stream transmitted from the local server to the at least one remote server and a plurality of audio latencies associated with audio data transmitted from the local server to the at least one remote server.

6. The hybrid media distribution system of claim 1,
wherein the at least one local media device comprises a telesurgery device,
wherein the at least one remote participant controls remote operation of the telesurgery device.

7. The hybrid media distribution system of claim 6, wherein at least one of the local server or the at least one remote server is further configured to:
restrict control of the remote operation of the telesurgery device in response to an increase in the second plurality of latencies.

8. One or more non-transitory computer-readable media storing computer-executable instructions that, when executed by at least one processor, perform a method of hybrid media distribution for telehealth sessions, comprising:
receiving, at a local server, local media data of a telehealth session from at least one local media device connected to the local server,
wherein the local server is disposed in a first location associated with a patient;
transmitting, by the local server, the local media data to at least one remote server operating on a remote network, the at least one remote server not disposed in the first location associated with the patient;
generating a native video recording of the local media data on the local server,
wherein the local media data comprises at least one first video stream;

responsive to receiving the local media data at the at least one remote server, broadcasting the local media data to one or more remote participants connected to the at least one remote server;
receiving, at the at least one remote server, telehealth session data from a remote participant from the one or more remote participants;
generating a remote video recording of the telehealth session data on the at least one remote server,
wherein the telehealth session data comprises at least one second video stream;
logging a first plurality of latencies between the local server and the at least one remote server;
logging a second plurality of latencies between the at least one remote server and the one or more remote participants; and
generating a synchronized recording of the telehealth session based on the native video recording, the remote video recording, the first plurality of latencies, and the second plurality of latencies,
wherein the synchronized recording includes the at least one first video stream from the native video recording and the at least one second video stream from the remote video recording, and
wherein the synchronized recording is synchronized to a time of data capture of the at least one first video stream by shifting in time the at least one second video stream based on at least one of the second plurality of latencies.

9. The media of claim 8, the method further comprising:
transmitting the telehealth session data from the at least one remote server to the local server; and
broadcasting the telehealth session data from the local server to at least one local client device connected to the local server.

10. The media of claim 8, wherein generating the synchronized recording comprises adjusting a remote video stream associated with the remote video recording based on the second plurality of latencies.

11. The media of claim 8, the method further comprising:
detecting an increase in the second plurality of latencies; and
transmitting, by the local server, a notification indicative of the increase in the second plurality of latencies to the one or more remote participants.

12. The media of claim 8, wherein the method further comprises:
prior to transmitting the local media data to the at least one remote server, applying, by the local server, an obscuration to at least a portion of the at least one first video stream.

13. The media of claim 12, the method further comprising:
logging a plurality of computational latencies; and
responsive to detecting an increase in the plurality of computational latencies, changing an obscuring method for obscuring the portion of the at least one first video stream.

14. A method for hybrid media distribution for a telehealth session, comprising:
receiving, at a local server operating on a hospital network, local media data of an operation being performed on a patient within a hospital associated with the hospital network;
transmitting the local media data to a remote server that is not disposed in the hospital;
responsive to receiving the local media data at the remote server, broadcasting, by the remote server, the local media data to a remote participant;
generating, on the local server, a first recording comprising the local media data,
wherein the local media data comprises at least one first video stream;
receiving remote telehealth session data from the remote participant at the remote server;
transmitting the remote telehealth session data to the local server;
generating, on the remote server, a second recording comprising the remote telehealth session data,
wherein the remote telehealth session data comprises at least one second video stream; and
generating a combined recording of the telehealth session based on the first recording and the second recording; and
synchronizing the combined recording by adjusting at least one of the first recording or the second recording based on a plurality of network latencies logged during the telehealth session,
wherein the combined recording includes the at least one first video stream from the first recording and the at least one second video stream from the second recording, and
wherein the combined recording is synchronized to a time of data capture of the at least one first video stream by shifting in time the at least one second video stream based on at least one of the plurality of network latencies.

15. The method of claim 14, wherein the first recording comprises a first frame rate higher than a second frame rate of the second recording.

16. The method of claim 15, wherein synchronizing the combined recording further comprises repeating frames from the second recording such that the second frame rate is increased to be equal to the first frame rate.

17. The method of claim 14, wherein the method further comprises:
prior to transmitting the local media data to the remote server, applying, by the local server, an obscuration to the at least one first video stream.

18. The method of claim 14, further comprising:
generating a third recording comprising data captured by a telesurgery device,
logging a third plurality of latencies associated with a plurality of log messages generated by the telesurgery device and transmitted to the local server,
wherein the combined recording further comprises the third recording, and
wherein synchronizing the combined recording is further based on the third plurality of latencies.

19. The method of claim 14,
wherein the local media data comprises at least one of audio data, video data, telestration data, telemetry data, or telesurgery data.

20. The method of claim 19,
wherein at least one of the local server or the remote server is configured to take a corrective action in response to an increase in a latency associated with the telesurgery data.

* * * * *